(12) United States Patent
Bouchon et al.

(10) Patent No.: US 7,683,076 B2
(45) Date of Patent: Mar. 23, 2010

US007683076B2

(54) TETRAHYDRO-QUINOLINYLUREA DERIVATIVES

(75) Inventors: Axel Bouchon, Köln (DE); Nicole Diedrichs, Velbert (DE); Achim Hermann, Düseldorf (DE); Klemens Lustig, Wuppertal (DE); Heinrich Meier, Wuppertal (DE); Josef Pernerstorfer, Hilden (DE); Elke Reißmüller, Wuppertal (DE); Muneto Mogi, Tsukuba (JP); Hiroshi Fujishima, Nara-ken (JP); Masaomi Tajimi, Aichi-ken (JP); Noriyuki Yamamoto, Osaka-fu (JP)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 327 days.

(21) Appl. No.: 10/578,413

(22) PCT Filed: Oct. 26, 2004

(86) PCT No.: PCT/EP2004/012051

§ 371 (c)(1),
(2), (4) Date: Jan. 19, 2007

(87) PCT Pub. No.: WO2005/044802

PCT Pub. Date: May 19, 2005

(65) Prior Publication Data

US 2007/0213363 A1    Sep. 13, 2007

(30) Foreign Application Priority Data

Nov. 8, 2003   (EP) .................................. 03025575

(51) Int. Cl.
  *C07D 215/38*   (2006.01)
  *A61K 31/47*    (2006.01)
(52) U.S. Cl. .................. 514/313; 514/314; 546/157; 546/163
(58) Field of Classification Search .................. 546/157, 546/163; 514/314, 313
  See application file for complete search history.

(56) References Cited

U.S. PATENT DOCUMENTS 6,984,647 B2 * 1/2006 Dax et al. .................... 514/307

FOREIGN PATENT DOCUMENTS

| WO | WO-99/00115 A1 | 1/1999 |
|---|---|---|
| WO | WO-00/29577 A1 | 5/2000 |
| WO | WO-00//50387 A1 | 8/2000 |
| WO | WO-03/014064 A1 | 2/2003 |
| WO | WO-03/022809 A2 | 3/2003 |
| WO | WO-03/053945 A2 | 7/2003 |
| WO | WO-03/070247 | 8/2003 |
| WO | WO-03/080578 A1 | 10/2003 |
| WO | WO-03/095420 | 11/2003 |
| WO | WO-2004/052845 | 6/2004 |
| WO | WO-2005/002551 | 1/2005 |

OTHER PUBLICATIONS

M. Tominaga et al.: "The Cloned Capsaicin Receptor Integrates Multiple Pain-Producing Stimuli," Neuron, vol. 21, Sep. 1998, pp. 531-543.
M. J. Caterina et al.: "The Capsaicin Receptor: a Heat-Activated Ion Channel in the Pain Pathway," Nature, vol. 389, Oct. 23, 1997, pp. 816-824.
W. De Groat: "A Neurologic Basis for the Overactive Bladder," Urology, vol. 50, Supp. 6A, 1997, pp. 36-52.
C. A. Maggi: "Therapeteutic Potential of Capsaicin-Like Molecules: Studies in Animals and Humans," Life Sciences, vol. 51, 1992, pp. 1777-1781.
D. D. Ridder et al.: "Intravesical Capsaicin as a Treatment for Refractory Detrusor Hyperreflexia - a Dual Center Study with Long-Term Follow Up," the Journal of Urology, vol. 158, Dec. 1997, pp. 2087-2092.
A. Lecci et al - Involvement in Spinal Tachykinin $NK_1$ and $NK_2$ Receptors in Detrusor Hyperreflexia during Chemical Cystitis in Anaesthetized Rats, European Journal of Pharmacology, vol. 259, 1994, pp. 129-135.

* cited by examiner

*Primary Examiner*—D. Margaret Seaman
(74) *Attorney, Agent, or Firm*—Edwards Angel Palmer & Dodge LLP; Nicholas J. DiCeglie, Jr.

(57) ABSTRACT

This invention relates to tetrahydro-quinolinylurea derivatives and salts thereof which are useful as active ingredients of pharmaceutical preparations. The tetrahydro-quinolinylurea derivative of the present invention has vanilloid receptor (VR1) antagonistic activity, and can be used for the prophylaxis and treatment of diseases associated with VR1 activity, in particular for the treatment of urological diseases or disorders, such as detrusor overactivity (overactive bladder), urinary incontinence, neurogenic detrusor overactivity (detrusor hyperflexia), idiopathic detrusor overactivity (detrusor instability), benign prostatic hyperplasia, and lower urinary tract symptoms; chronic pain, neuropathic pain, postoperative pain, rheumatoid arthritic pain, neuralgia, neuropathies, algesia, nerve injury, ischaemia, neurodegeneration, stroke, and inflammatory disorders such as asthma and chronic obstructive pulmonary (or airways) disease (COPD).

15 Claims, No Drawings

TETRAHYDRO-QUINOLINYLUREA DERIVATIVES

This application is a 371 of PCT/EP2004/012051, filed Oct. 26, 2004.

DETAILED DESCRIPTION OF INVENTION

1. Technical Field

The present invention relates to a tetrahydro-quinolinylurea derivative which is useful as an active ingredient of pharmaceutical preparations. The tetrahydro-quinolinylurea derivative of the present invention has vanilloid receptor (VR1) antagonistic activity, and can be used for the prophylaxis and treatment of diseases associated with VR1 activity, in particular for the treatment of urological diseases or disorders, such as detrusor overactivity (overactive bladder), urinary incontinence, neurogenic detrusor overactivity (detrusor hyperflexia), idiopathic detrusor overactivity (detrusor instability), benign prostatic hyperplasia, and lower urinary tract symptoms; chronic pain, neuropathic pain, postoperative pain, rheumatoid arthritic pain, neuralgia, neuropathies, algesia, nerve injury, ischemia, neurodegeneration, stroke, and inflammatory disorders such as asthma and chronic obstructive pulmonary (or airways) disease (COPD).

2. Background Art

Vanilloid compounds are characterized by the presence of vanillyl group or a functionally equivalent group. Examples of several vanilloid compounds or vanilloid receptor modulators are vanillin (4-hydroxy-3-methoxy-benzaldehyde), guaiacol (2-methoxy-phenol), zingerone (4-/4-hydroxy-3-methoxyphenyl/-2-butanone), eugenol (2-methoxy-4-/2-propenyl/phenol), and capsaicin (8-methyl-N-vanillyl-6-noneneamide).

Among others, capsaicin, the main pungent ingredient in "hot" chili peppers, is a specific neurotoxin that desensitizes C-fiber afferent neurons. Capsaicin interacts with vanilloid receptors (VR1), which are predominantly expressed in cell bodies of dorsal root ganglia (DRG) or nerve endings of afferent sensory fibers including C-fiber nerve endings [Tominaga M, Caterina M J, Malmberg A B, Rosen T A, Gilbert H, Skinner K, Raumann B E, Basbaum A I, Julius D: The cloned capsaicin receptor integrates multiple pain-producing stimuli. Neuron. 21: 531-543, 1998]. The VR1 receptor was recently cloned [Caterina M J, Schumacher M A, Tominaga M, Rosen T A, Levine J D, Julius D: Nature 389: 816-824, (1997)] and identified as a nonselective cation channel with six transmembrane domains that is structurally related to the TRP (transient receptor potential) channel family. Binding of capsaicin to VR1 allows sodium, calcium and possibly potassium ions to flow down their concentration gradients, causing initial depolarization and release of neurotransmitters from the nerve terminals. VR1 can therefore be viewed as a molecular integrator of chemical and physical stimuli that elicit neuronal signals in pathological conditions or diseases.

There is abundant direct or indirect evidence that shows the relation between VR1 activity and diseases such as pain, ischemia, and inflammatory disorders (e.g., WO 99/00115 and 00/50387). Further, it has been demonstrated that VR1 transduces reflex signals that are involved in the overactive bladder of patients who have damaged or abnormal spinal reflex pathways [De Groat W C: A neurologic basis for the overactive bladder. Urology 50 (6A Suppl): 36-52, 1997]. Desensitisation of the afferent nerves by depleting neurotransmitters using VR1 agonists such as capsaicin has been shown to give promising results in the treatment of bladder dysfunction associated with spinal cord injury and multiple sclerosis [Maggi C A: Therapeutic potential of capsaicin-like molecules—Studies in animals and humans. Life Sciences 51: 1777-1781, 1992) and (DeRidder D; Chandiramani V; Dasgupta P; VanPoppel H; Baert L; Fowler C J: Intravesical capsaicin as a treatment for refractory detrusor hyperreflexia: A dual center study with long-term followup. J. Urol. 158: 2087-2092, 1997)].

It is anticipated that antagonism of the VR1 receptor would lead to the blockage of neuro-transmitter release, resulting in prophylaxis and treatment of the conditions and diseases associated with VR1 activity.

It is therefore expected that antagonists of the VR1 receptor can be used for prophylaxis and treatment of the conditions and diseases including chronic pain, neuropathic pain, postoperative pain, rheumatoid arthritic pain, neuralgia, neuropathies, algesia, nerve injury, ischemia, neuro-degeneration, stroke, inflammatory disorders, urinary incontinence (UI) such as urge urinary incontinence (UUI), and/or overactive bladder.

UI is the involuntary loss of urine. UUI is one of the most common types of UI together with stress urinary incontinence (SUI) which is usually caused by a defect in the urethral closure mechanism. UUI is often associated with neurological disorders or diseases causing neuronal damages such as dementia, Parkinson's disease, multiple sclerosis, stroke and diabetes, although it also occurs in individuals with no such disorders. One of the usual causes of UUI is overactive bladder (OAB) which is a medical condition referring to the symptoms of frequency and urgency derived from abnormal contractions and instability of the detrusor muscle.

There are several medications for urinary incontinence on the market today mainly to help treating UUI. Therapy for OAB is focused on drugs that affect peripheral neural control mechanisms or those that act directly on bladder detrusor smooth muscle contraction, with a major emphasis on development of anticholinergic agents. These agents can inhibit the parasympathetic nerves which control bladder voiding or can exert a direct spasmolytic effect on the detrusor muscle of the bladder. This results in a decrease in intravesicular pressure, an increase in capacity and a reduction in the frequency of bladder contraction. Orally active anticholinergic drugs which are commonly prescribed have serious drawbacks such as unacceptable side effects such as dry mouth, abnormal visions, constipation, and central nervous system disturbances. These side effects lead to poor compliance. Dry mouth symptoms alone are responsible for a 70% non-compliance rate with oxybutynin. The inadequacies of present therapies highlight the need for novel, efficacious, safe, orally available drugs that have fewer side effects.

WO03/014064 discloses the compounds represented by the general formula:

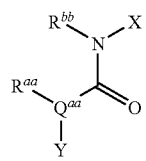

wherein
X represents $C_{3-8}$ cycloalkyl optionally fused by benzene, optionally substituted naphthyl, optionally substituted phenyl, optionally substituted phenyl $C_{1-6}$ straight alkyl, phenyl fused by cycloalykyl, etc;
$Q^{aa}$ represents CH or N;
$R^{aa}$ represents hydrogen or methyl;
$R^{bb}$ represents hydrogen or methyl; and
Y represents substituted naphthyl,
as a vanilloid receptor antagonist.

WO03/022809 discloses the compounds having vanilloid receptor antagonist activity represented by the general formula:

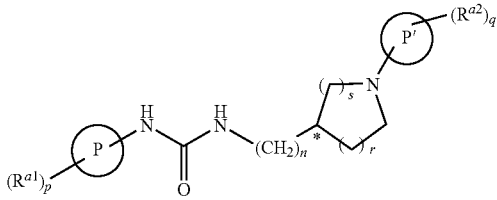

wherein
P and P' independently represent aryl or heteroaryl;
$R^{a1}$ and $R^{a2}$ independently represent hydrogen, alkoxy, hydroxy, etc;
n is 0, 1, 2 or 3; p and q are independently 0, 1, 2, 3 or 4; r is 1, 2 or 3; and s is 0, 1 or 2.

WO03/053945 discloses the compounds having vanilloid receptor antagonist activity represented by the general formula:

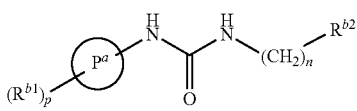

wherein
$P^a$ represents phenyl, naphthyl or heterocyclyl;
n is 2, 3, 4, 5 or 6; p is independently 0, 1, 2, 3 or 4;
$R^{b1}$ represents hydrogen, alkoxy, hydroxy, etc; and
$R^{a2}$ represents

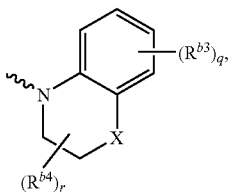

wherein X is a bond, C, O, or $NR^{b8}$; and r, q, $R^{b3}$, $R^{b4}$ are defined in the application.

WO03/070247 discloses the compounds having vanilloid receptor antagonist activity represented by the general formula:

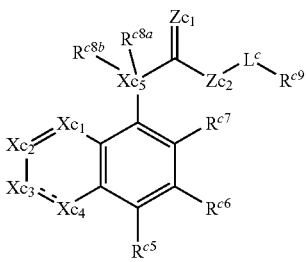

wherein
$Xc_1$ represents N or $CR^{c1}$; $Xc_2$ represents N or $CR^{c2}$; $Xc_3$ represents N, $NR^{c3}$ or $CR^{c3}$; $Xc_4$ represents a bond, N or $CR^{c4}$; $Xc_5$ represents N or C; provided that at least one of $Xc_1, Xc_2, Xc_3$ and $Xc_4$ is N; $Zc_1$ represents O, NH or S; $Zc_2$ represents a bond, NH or S; $L^c$ represents alkylene, cycloalkylene, etc; $R^{c1}, R^{c2}, R^{c3}, R^{c4}, R^{c5}, R^{c6}, R^{c7}, R^{c8a}$ $R^{c8b}$ are defined in the application; and $R^{c9}$ represents hydrogen, aryl, cycloalkyl, and heterocylcle.

WO03/080578 discloses the compounds having vanilloid receptor antagonist activity represented by the general formula:

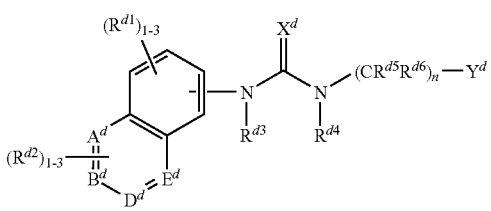

wherein
$A^d, B^d, D^d$ and $E^d$ are each C or N with the proviso that one or more are N; $X^d$ is an O, S or $=NCN$;
$Y^d$ is an aryl, heteroaryl, carbocyclyl or fused-carbocyclyl; n is 0, 1, 2 or 3; and $R^{d1}, R^{d2}, R^{d3}, R^{d4}, R^{d5}$ and $R^{d6}$ are defined in the application.

The development of a compound which has effective VR1 antagonistic activity and can be used for the prophylaxis and treatment of diseases associated with VR1 activity, in particular for the treatment of urinary incontinence, urge urinary incontinence, overactive bladder as well as pain, and/or inflammatory diseases such as asthma and COPD has been desired.

SUMMARY OF THE INVENTION

This invention is to provide a urea derivative of the formula (I), their tautomeric and stereoisomeric form, and salts thereof:

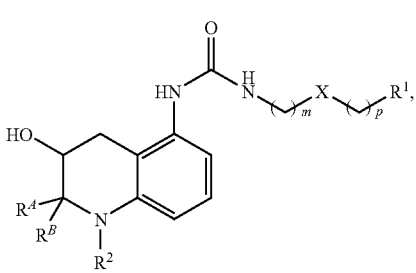

(I)

wherein
m represents 0, 1, 2, or 3;
p represents 0, 1, 2, or 3;
—X— represents bond, —O— or —N($R^{10}$)— (wherein $R^{10}$ is hydrogen or $C_{1-6}$ alkyl);
with the proviso that when m is 0, —X— represents a bond,
$R^A$ and $R^B$ represent hydrogen, or
$R^A$ and $R^B$ together form a carbonyl-group with the carbon-atom to which they are connected,
$R^1$ represents aryl or heteroaryl wherein said aryl and heteroaryl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle; and $R^2$ represents $C_{1-6}$alkylcarbonyl, $C_{1-6}$alkylsulfonyl, hydrogen, hydroxy,
aryl, heteroaryl, $C_{1-6}$alkyl, $C_{2-6}$alkenyl, $C_{2-6}$-alkynyl, $C_{3-8}$cycloalkyl, arylsulfonyl, or heteroarylsulfonyl,
wherein
said allyl, alkenyl or alkynyl are optionally substituted by mono-, di-, or tri-halogen, hydroxy, carboxyl, nitro, cyano, $C_{1-6}$alkoxy, $C_{1-6}$alkoxycarbonyl, $C_{3-8}$-cycloalkyl, amino, N—$C_{1-6}$alkyl)amino, N,N-di($C_{1-6}$-alkyl)amino, N-(aryl)amino, N-(heteroaryl)amino, carbamoyl, N—($C_{1-6}$alkyl)aminocarbonyl, or N,N,-di($C_{1-6}$alkyl)-aminocarbonyl, and
said cycloalkyl, aryl, heteroaryl, aryl moiety of said arylsulfonyl, or heteroaryl moiety of said heteroarylsulfonyl are optionally substituted by
mono-, di-, or tri-halogen, hydroxy, carboxyl, cyano, nitro, ($C_{1-6}$alkoxy)carbonyl, $C_{3-8}$cycloalkyl, amino, N—($C_{1-6}$ alkyl)amino, N,N-di($C_{1-6}$alkyl)amino, N-(aryl)amino, N-(heteroaryl)amino, carbamoyl, N—($C_{1-6}$alkyl)aminocarbonyl, N,N-di($C_{1-6}$alkyl)-aminocarbonyl, $C_{1-6}$alkyl optionally substituted by mono-, di-, or tri-halogen, or $C_{1-6}$alkoxy optionally substituted by mono-, di-, or tri-halogen.

In another embodiment, the urea derivative of formula (I) can be those wherein;
wherein
m represents 0, 1, 2, or 3;
p represents 0, 1, 2, or 3;
—X— represents bond, —O— or —N($R^{10}$)— (wherein $R^{10}$ is hydrogen or $C_{1-6}$ alkyl);
with the proviso that when m is 0, —X— represents a bond,
$R^A$ and $R^B$ represent hydrogen,
$R^1$ represents aryl or heteroaryl
wherein said aryl and heteroaryl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxy-carbonyl or $C_{1-6}$ alkyl), $C_{1-6}$ alkylthio (which alkylthio is optionally substituted by mono-, di-, or tri-halogen), $C_{3-8}$ cycloalkyl, and heterocycle; and $R^2$ represents $C_{1-6}$alkylcarbonyl, $C_{1-6}$alkylsulfonyl, hydrogen, hydroxy,
aryl, heteroaryl, $C_{1-6}$alkyl, $C_{2-6}$alkenyl, $C_{2-6}$-alkynyl, $C_{3-8}$cycloalkyl, arylsulfonyl, or heteroarylsulfonyl,
wherein
said allyl, alkenyl or alkynyl are optionally substituted by mono-, di-, or tri-halogen, hydroxy, carboxyl, nitro, cyano, $C_{1-6}$alkoxy, $C_{1-6}$alkoxycarbonyl, $C_{3-8}$-cycloalkyl, amino, N—$C_{1-6}$alkyl)amino, N,N-di($C_{1-6}$-alkyl)amino, N-(aryl)amino, N-(heteroaryl)amino, carbamoyl, N—($C_{1-6}$alkyl)aminocarbonyl, or N,N,-di($C_{1-6}$alkyl)-aminocarbonyl, and
said cycloalkyl, aryl, heteroaryl, aryl moiety of said arylsulfonyl, or heteroaryl moiety of said heteroarylsulfonyl are optionally substituted by
mono-, di-, or tri-halogen, hydroxy, carboxyl, cyano, nitro, ($C_{1-6}$alkoxy)carbonyl, $C_{3-8}$cycloalkyl, amino, N—($C_{1-6}$ alkyl)amino, N,N-di($C_{1-6}$alkyl)amino, N-(aryl)amino, N-(heteroaryl)amino, carbamoyl, N—($C_{1-6}$alkyl)aminocarbonyl, N,N-di($C_{1-6}$alkyl)-aminocarbonyl, $C_{1-6}$alkyl optionally substituted by mono-, di-, or tri-halogen, or $C_{1-6}$alkoxy optionally substituted by mono-, di-, or tri-halogen.

In another embodiment, the urea derivative of formula (I) can be those wherein;
wherein
m represents 0, 1, 2, or 3;
p represents 0, 1, 2, or 3;
—X— represents bond, —O— or —N($R^{10}$)— (wherein $R^{10}$ is hydrogen or $C_{1-6}$ alkyl);
with the proviso that when m is 0, —X— represents a bond,
$R^A$ and $R^B$ represent hydrogen,
$R^1$ represents phenyl, naphthyl, pyridyl, or pyrimidyl,
wherein
said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle $R^2$ represents $C_{1-6}$alkylcarbonyl, $C_{1-6}$alkylsulfonyl, hydrogen, hydroxy, aryl, heteroaryl, $C_{1-6}$alkyl, $C_{2-6}$alkenyl, $C_{2-6}$alynyl, $C_{3-8}$cycloalkyl, arylsulfonyl, or heteroarylsulfonyl, wherein said alkyl, alkenyl or alkynyl are optionally substituted by mono-, di-, or tri-halogen, hydroxy, carboxyl, nitro, cyano, $C_{1-6}$alkoxy, $C_{1-6}$alkoxycarbonyl, $C_{3-8}$cycloalkyl, amino, N—($C_{1-6}$alkyl)amino, N,N-di($C_{1-6}$alkyl)amino, N-(aryl)amino, N-heteroaryl)amino, carbamoyl, N—($C_{1-6}$alkyl)aminocarbonyl, or N,N,-di-($C_{1-6}$alkyl)aminocarbonyl, and said cycloalkyl, aryl, heteroaryl, aryl moiety of said arylsulfonyl, or heteroaryl moiety of said heteroarylsulfonyl are optionally substituted by mono-, di-, or tri-halogen, hydroxy, carboxyl, cyano, nitro, ($C_{1-6}$alkoxy)carbonyl, $C_{3-8}$cycloalkyl, amino, N—($C_{1-6}$-alkyl)amino, N,N-di($C_{1-6}$alkyl)amino, N-(aryl)amino, N-heteroaryl)amino, carbamoyl, N—($C_{1-6}$alkyl)aminocarbonyl, N,N-di($C_{1-6}$alkyl)-aminocarbonyl, $C_{1-6}$alkyl optionally substituted by mono-, di-, or tri-halogen, or $C_{1-6}$alkoxy optionally substituted by mono-, di-, or tri-halogen.

In another embodiment, the urea derivative of formula (I) can be those wherein;

wherein m represents 0, 1, 2, or 3;

p represents 0, 1, 2, or 3;

—X— represents bond, —O— or —N($R^{10}$)— (wherein $R^{10}$ is hydrogen or $C_{1-6}$ alkyl);

with the proviso that when m is 0, —X— represents a bond, $R^A$ and $R^B$ represent hydrogen, $R^1$ represents phenyl, naphthyl, pyridyl, or pyrimidyl, wherein said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle $R^2$ represents $C_{1-6}$alkylcarbonyl, $C_{1-6}$alkylsulfonyl, hydrogen, hydroxy, phenyl, naphthyl, pyridyl, or pyrimidyl, $C_{1-6}$alkyl, $C_{2-6}$alkenyl, $C_{2-6}$alkynyl, $C_{3-8}$cycloalkyl, phenysulfonyl, pyrimidylsulfonyl, or pyridylsulfonyl, wherein said alkyl, alkenyl or alkynyl are optionally substituted by mono-, di-, or tri-halogen, hydroxy, carboxyl, nitro, cyano, $C_{1-6}$alkoxy, $C_{1-6}$alkoxycarbonyl, $C_{3-8}$cycloalkyl, amino, N—($C_{1-6}$alkyl)amino, N,N-di($C_{1-6}$alkyl)amino, N-(aryl)amino, N-(heteroaryl)amino, carbamoyl, N—($C_{1-6}$alkyl)aminocarbonyl, or N,N,-di-($C_{1-6}$alkyl)aminocarbonyl, and said cycloalkyl, phenyl, naphthyl, pyridyl, pyrimidyl, phenyl moiety, pyridyl moiety or pyrimidyl moiety of said phenylsulfonyl, pyridylsulfonyl, pyrimidylsulfonyl are optionally substituted by mono-, di-, or tri-halogen, hydroxy, carboxyl, cyano, nitro, ($C_{1-6}$alkoxy)carbonyl, $C_{3-8}$cycloalkyl, amino, N—($C_{1-6}$-alkyl)amino, N,N-di($C_{1-6}$alkyl)amino, N-(aryl)amino, N-(heteroaryl)amino, carbamoyl, N—($C_{1-6}$alkyl)aminocarbonyl, N,N-di($C_{1-6}$alkyl) aminocarbonyl, $C_{1-6}$alkyl optionally substituted by mono-, di-, or tri-halogen, or $C_{1-6}$alkoxy optionally substituted by mono-, di-, or tri-halogen.

In a further embodiment, said urea derivative of the formula (I) can be those wherein;

wherein m represents 0, 1, 2, or 3;

p represents 0;

—X— represents bond;

$R^A$ and $R^B$ represent hydrogen, $R^1$ represents phenyl, naphthyl, pyridyl, or pyrimidyl, wherein said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle $R^2$ represents $C_{1-6}$alkylcarbonyl, $C_{1-6}$alkylsulfonyl, hydrogen, hydroxy, phenyl, naphthyl, pyridyl, or pyrimidyl, $C_{1-6}$alkyl, $C_{2-6}$alkenyl, $C_{2-6}$alkynyl, $C_{3-8}$-cycloalkyl, phenysulfonyl, pyrimidylsulfonyl, or pyridylsulfonyl, wherein
said alkyl, alkenyl or alkynyl are optionally substituted by mono-, di-, or tri-halogen, hydroxy, carboxyl, nitro, cyano, $C_{1-6}$alkoxy, $C_{1-6}$alkoxycarbonyl, $C_{3-8}$cycloalkyl, amino, N—($C_{1-6}$alkyl)amino, N,N-di($C_{1-6}$ alkyl)amino, N-(aryl)amino, N-(heteroaryl)amino, carbamoyl, N—($C_{1-6}$alkyl)aminocarbonyl, or N,N,-di($C_{1-6}$alkyl)-aminocarbonyl, and
said cycloalkyl, phenyl, naphthyl, pyridyl, pyrimidyl, phenyl moiety, pyridyl moiety or pyrimidyl moiety of said phenylsulfonyl, pyridylsulfonyl, pyrimnidylsulfonyl are optionally substituted by
mono-, di-, or tri-halogen, hydroxy, carboxyl, cyano, nitro, ($C_{1-6}$alkoxy)carbonyl, $C_{3-8}$cycloalkyl, amino, N—($C_{1-6}$alkyl)amino, N,N-di($C_{1-6}$alkyl)amino, N-(aryl)amino, N-(heteroaryl)amino, carbamoyl, N—($C_{1-6}$-alkyl)aminocarbonyl, N,N-di($C_{1-6}$alkyl)aminocarbonyl, $C_{1-6}$alkyl optionally substituted by mono-, di-, or tri-halogen, or $C_{1-6}$alkoxy optionally substituted by mono-, di-, or tri-halogen.

Yet in a further embodiment, said urea derivative of the formula (I) can be those wherein:
wherein
m represents 1,2, or 3;
p represents 0, 1, 2, or 3;
—X— represents bond, —O— or —N($R^{10}$)— (wherein $R^{10}$ is hydrogen or $C_{1-6}$alkyl);
$R^A$ and $R^B$ represent hydrogen,
$R^1$ represents phenyl, naphthyl, pyridyl, or pyrimidyl,
wherein
said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$alkylamino, di($C_1$-alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle
$R^2$ represents $C_{1-6}$alkylcarbonyl, $C_{1-6}$alkylsulfonyl, hydrogen, hydroxy, $C_{1-6}$alkyl, $C_{2-6}$-alkenyl, $C_{2-6}$alkynyl, $C_{3-8}$cycloalkyl,
wherein
said alkyl, alkenyl cycloalkyl, or alkynyl are optionally substituted by mono-, di-, or tri-halogen, hydroxy, carboxyl, nitro, cyano, $C_{1-6}$alkoxy, $C_{1-6}$alkoxycarbonyl, $C_{3-8}$cycloalkyl, amino, N—$C_{1-6}$alkyl)amino, N,N-di($C_{1-6}$alkyl)amino, N-(aryl)amino, N-(heteroaryl)amino, carbamoyl, N—($C_{1-6}$alkyl)aminocarbonyl, or N,N,-di($C_{1-6}$alkyl)aminocarbonyl.

In a further embodiment, said urea derivative of the formula (I) can be those wherein:
wherein
m represents 0;
p represents 0;
—X— represents —O— or —N($R^{10}$)— (wherein $R^{10}$ is hydrogen or $C_{1-6}$ alkyl);
$R^A$ and $R^B$ represent hydrogen,
$R^1$ represents phenyl, naphthyl, pyridyl, or pyrimidyl,
wherein
said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle
$R^2$ represent $C_{1-6}$alkylcarbonyl, $C_{1-6}$alkylsulfonyl, hydrogen, hydroxy, $C_{1-6}$alkyl, $C_{2-6}$-alkenyl, $C_{2-6}$alkynyl, $C_{3-8}$cycloalkyl,
wherein said alkyl, alkenyl cycloalkyl, or alkynyl are optionally substituted by
mono-, di-, or tri-halogen, hydroxy, carboxyl, nitro, cyano, $C_{1-6}$alkoxy, $C_{1-6}$alkoxy-carbonyl, $C_{3-8}$cycloalkyl, amino, N—($C_{1-6}$-alkyl)amino, N,N-di($C_{1-6}$ alkyl)amino, N-(aryl)amino, N-(heteroaryl)amino, carbamoyl, N—($C_{1-6}$alkyl)aminocarbonyl, or N,N,-di($C_{1-6}$alkyl)aminocarbonyl.

Yet in a further embodiment, said urea derivative of the formula (I) can be those wherein:
wherein
m represents 1,2, or 3;
p represents 0, 1, 2, or 3;
—X— represents bond, —O— or —N($R^{10}$)— (wherein $R^{10}$ is hydrogen or $C_{1-6}$ alkyl);
$R^A$ and $R^B$ represent hydrogen,
$R^1$ represents phenyl, naphthyl, pyridyl, or pyrimidyl,
wherein
said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$alkoxycarbonyl, phenyl (which phenyl is optionally substituted by halogen, nitro, hydroxy, carboxy, amino, $C_{1-6}$ alkylamino, di($C_{1-6}$alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{1-6}$ cycloalkyl, and heterocycle $R^2$ represents hydrogen, hydroxy, $C_{1-6}$alkyl, $C_{2-6}$alkenyl, $C_{2-6}$alkynyl, $C_{3-8}$cycloalkyl, Yet in a further embodiment, said urea derivative of the formula (I) can be those
wherein $R^1$ represents phenyl, naphthyl, pyridyl, or pyrimidyl,
wherein said phenyl, naphthyl, pyridyl, or pyrimidyl is optionally substituted by one or more of substituents selected from the group consisting of chloro, bromo, fluoro, nitro, methoxy, trifluoromethyl, trifluoromethoxy and $C_{1-6}$ alkanoylamino.

Preferably, said urea derivative of the formula (I) is selected from the group consisting of:

N-(4-chlorophenyl)-N'-(3-hydroxy-1-methyl-,1,2,3,4-tetrahydroquinolin-5-yl)urea;

N-[4-chloro-3-(trifluoromethyl)phenyl]-N'-(3-hydroxy-1-methyl-1,2,3,4-tetrahydroquinolin-5-yl)urea;

N-[4-chloro-3-(trifluoromethyl)phenyl]-N'-(3-hydroxy-1,2,3,4-tetrahydroquinolin-5-yl)urea;

ethyl 3-({[(3-hydroxy-1-methyl-1,2,3,4-tetrahydroquinolin-5-yl)amino]carbonyl}amino)benzoate; and N-biphenyl-3-yl-N'-(3-hydroxy-1-methyl-1,2,3,4-tetrahydroquinolin-5-yl)urea.

The tetrahydro-quinolinylurea derivatives of formula (I), their tautomeric and stereoisomeric form, and salts thereof surprisingly show excellent VR1 antagonistic activity. They are, therefore suitable especially for the prophylaxis and treatment of diseases associated with VR1 activity, in particular for the treatment of urological diseases or disorders, such as detrusor overactivity (overactive bladder), urinary incontinence, neurogenic detrusor overactivity (detrusor hyperflexia), idiopathic detrusor overactivity (detrusor instability), benign prostatic hyperplasia, and lower urinary tract symptoms.

The compounds of the present invention are also effective for treating or preventing a disease selected from the group consisting of chronic pain, neuropathic pain, postoperative pain, rheumatoid arthritic pain, neuralgia, neuropathies, algesia, nerve injury, ischaemia, neuro-degeneration and/or stroke, as well as inflammatory diseases such as asthma and COPD since the diseases also relate to VR1 activity.

The compounds of the present invention are also useful for the treatment and prophylaxis of neuropathic pain, which is a form of pain often associated with herpes zoster and postherpetic neuralgia, painful diabetic neuropathy, neuropathic low back pain, posttraumatic and postoperative neuralgia, neuralgia due to nerve compression and other neuralgias, phantom pain, complex regional pain syndromes, infectious or parainfectious neuropathies like those associated with HIV infection, pain associated with central nervous system disorders like multiple sclerosis or Parkinson disease or spinal cord injury or traumatic brain injury, and post-stroke pain.

Furthermore, the compounds of the present invention are useful for the treatment of musculo-skeletal pain, forms of pain often associated with osteoarthritis or rheumatoid arthritis or other forms of arthritis, and back pain.

In addition, the compounds of the present invention are useful for the treatment of pain associated with cancer, including visceral or neuropathic pain associated with cancer or cancer treatment.

The compounds of the present invention are furthermore useful for the treatment of visceral pain, e.g. pain associated with obstruction of hollow viscus like gallstone colik, pain associated with irritable bowel syndrome, pelvic pain, vulvodynia, orchialgia or prostatodynia, pain associated with inflammatory lesions of joints, skin, muscles or nerves, and orofascial pain and headache, e.g. migraine or tension-type headache.

Further, the present invention provides a medicament, which includes one of the compounds, described above and optionally pharmaceutically acceptable excipients.

Alkyl per se and "alk" and "alkyl" in alkenyl, alkynyl, alkoxy, alkanoyl, alkylamino, alkylamino-carbonyl, alkylaminosulfonyl, alkylsulfonylamino, alkoxycarbonyl, alkoxycarbonylamino and alkanoylamino represent a linear or branched alkyl radical having generally 1 to 6, preferably 1 to 4 and particularly preferably 1 to 3 carbon atoms, representing illustratively and preferably methyl, ethyl, n-propyl, isopropyl, tert-butyl, n-pentyl and n-hexyl.

Alkoxy illustratively and preferably represents methoxy, ethoxy, n-propoxy, isopropoxy, tert-butoxy, n-pentoxy and n-hexoxy.

Alkylamino illustratively and preferably represents an alkylamino radical having one or two (independently selected) alkyl substituents, illustratively and preferably representing methylamino, ethylamino, n-propylamino, isopropylamino, tert-butylamino, n-pentylamino, n-hexyl-amino, N,N-dimethylamino, N,N-diethylamino, N-ethyl-N-methylamino, N-methyl-N-n-propylamino, N-iso-propyl-N-n-propylamino, N-t-butyl-N-methylamino, N-ethyl-N-n-pentylamino and N-n-hexyl-N-methylamino.

Aryl per se and in arylamino and in arylcarbonyl represents a mono- to tricyclic aromatic carbocyclic radical having generally 6 to 14 carbon atoms, illustratively and preferably representing phenyl, naphthyl and phenanthrenyl.

Cycloalkyl per se and in cycloalkylamino and in cycloalkylcarbonyl represents a cycloalkyl group having generally 3 to 8 and preferably 5 to 7 carbon atoms, illustratively and preferably representing cyclopropyl, cyclobutyl, cyclopentyl, cyclohexyl and cycloheptyl.

Heteroaryl per se and the heteroaryl portion of the heteroaralkyl, heteroaryloxy, heteroaralkyloxy, or heteroarylcarbamoyl represent an aromatic mono- or bicyclic radical having generally 5 to 10 and preferably 5 or 6 ring atoms and up to 5 and preferably up to 4 hetero atoms selected from the group consisting of S, O and N, illustratively and preferably representing thienyl, furyl, pyrrolyl, thiazolyl, oxazolyl, imidazolyl, pyridyl, pyrimidyl, pyridazinyl, indolyl, isoindolino, indazolyl, benzofuranyl, benzothiophenyl, quinolinyl, isoquinolinyl, tetrazolyl, and triazolyl.

Heterocyclyl per se and in heterocyclylcarbonyl represents a mono- or polycyclic, preferably mono- or bicyclic, nonaromatic heterocyclic radical having generally 4 to 10 and preferably 5 to 8 ring atoms and up to 3 and preferably up to 2 hetero atoms and/or hetero groups selected from the group consisting of N, O, S, SO and $SO_2$. The heterocyclyl radicals can be saturated or partially unsaturated. Preference is given to 5- to 8-membered monocyclic saturated heterocyclyl radicals having up to two hetero atoms selected from the group consisting of O, N and S, such as illustratively and preferably 1,3-dioxalanyl, tetrahydrofuran-2-yl, pyrrolidin-2-yl, pyrrolidin-3-yl, pyrrolinyl, piperidinyl, morpholinyl, perhydroazepinyl.

EMBODIMENT OF THE INVENTION

The compound of the formula (I) of the present invention can be, but not limited to be, prepared by combining various known methods. In some embodiments, one or more of the substituents, such as amino group, carboxyl group, and hydroxyl group of the compounds used as starting materials or intermediates are advantageously protected by a protecting group known to those skilled in the art. Examples of the protecting groups are described in "Protective Groups in Organic Synthesis (3rd Edition)" by Greene and Wuts, John Wiley and Sons, New York 1999.

The compound of the formula (I) of the present invention can be, but not limited to be, prepared by the Method [A], [B], [C], [D], or [E] below.

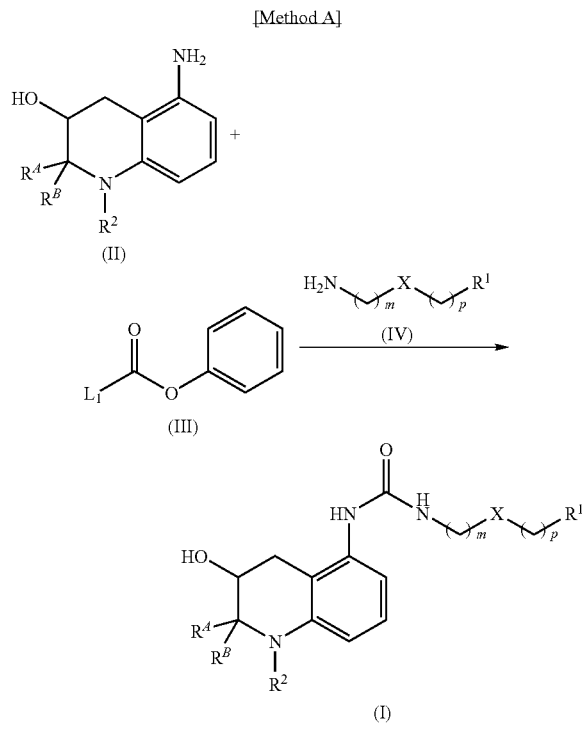

The compound of the formula (I) (wherein m, p, $R^A$, $R^B$, $R^1$, $R^2$ and X are the same as defined above) can be prepared by reacting the compound of the formula (II) (wherein $R^A$, $R^B$ and $R^2$ are the same as defined above) and the compound of the formula (III) (wherein $L_1$ represents a leaving group including halogen atom such as chlorine, bromine, or iodine atom) and then adding the compound of the formula (IV) (wherein m, p, $R^1$ and X are the same as defined above) to the reaction mixture.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2 dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 20° C. to 50° C. The reaction may be conducted for, usually, 30 minutes to 24 hours and preferably 1 to 10 hours.

The reaction can be advantageously carried out in the presence of a base including, for instance, organic amines such as pyridine, triethylamine and N,N-diisopropylethylamine, dimethylaniline, diethylaniline, 4-dimethylaminopyridine, and others.

The compound of the formula (III) and (IV) are commercially available or can be prepared by the use of known techniques.

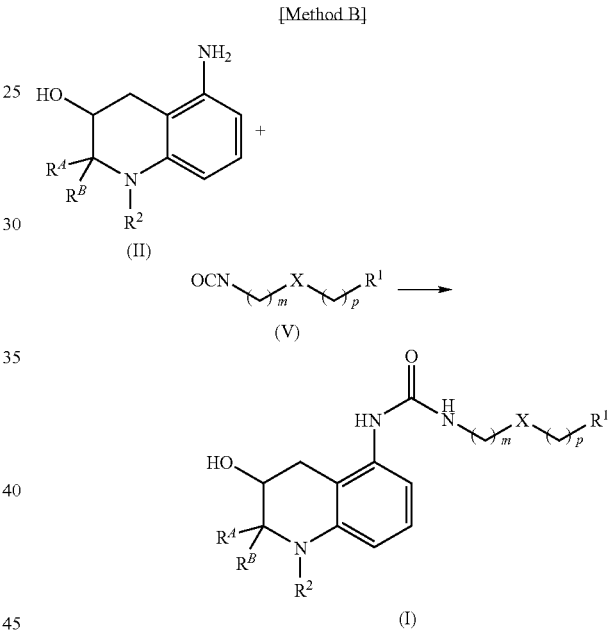

The compound of the formula (I) (wherein m, p, $R^A$, $R^B$, $R^1$, $R^2$ and X are the same as defined above) can be prepared by the reaction of the compound of the formula (II) (wherein $R^A$, $R^B$ and $R^2$ are the same as defined above) and the compound of the formula (V) (wherein m, p, $R^1$ and X are the same as defined above).

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction can be carried out in the presence of organic base such as pyridine or triethylamine.

The reaction temperature can be optionally set depending on the compounds to be reacted. The reaction temperature is usually, but not limited to, about room temperature to 100° C. The reaction may be conducted for, usually, 30 minutes to 24 hours and preferably 1 to 10 hours.

The compound (V) can be prepared by the use of known techniques or are commercially available.

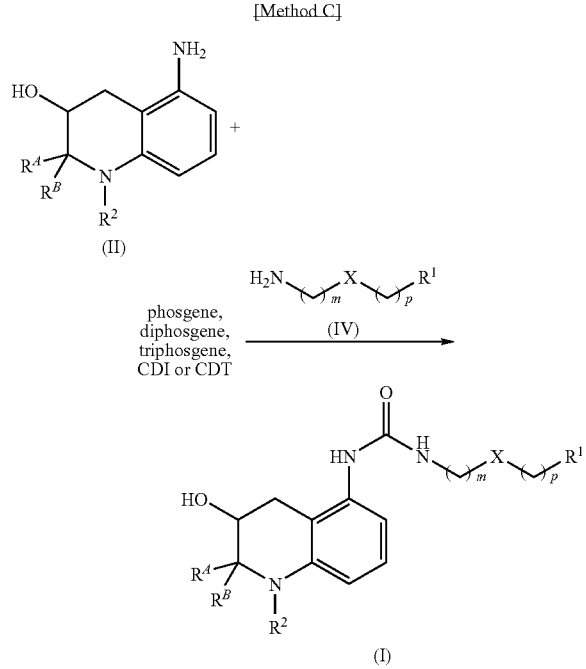

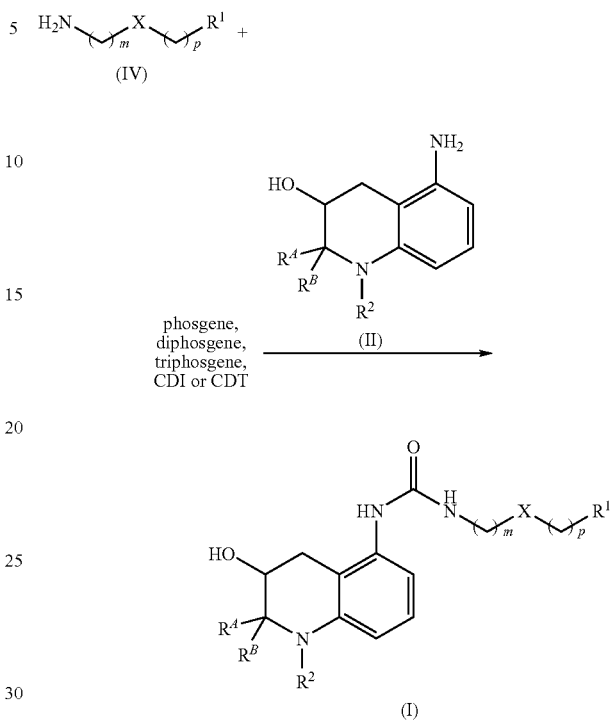

The compound of the formula (I) (wherein m, p, $R^A$, $R^B$, $R^1$, $R^2$ and X are the same as defined above) can be prepared by reacting the compound of the formula (II) (wherein $R^A$, $R^B$ and $R^2$ are the same as defined above) with phosgene, diphosgene, triphosgene, 1,1-carbonyldiimidazole (CDI), or 1,1'-carbonyldi(1,2,4-triazole)(CDT), and then adding the compound of the formula (IV) (wherein m, p, $R^1$ and X are the same as defined above) to the reaction mixture.

The reaction may be carried out in a solvent including, for instance, halogenated hydrocarbons such as dichloromethane, chloroform and 1,2-dichloroethane; ethers such as diethyl ether, iso-propyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 20° C. to 50° C. The reaction may be conducted for, usually, 30 minutes to 24 hours and preferably 1 to 10 hours.

Phosgene, diphosgene, triphosgene, CDI, and CDT are commercially available.

The compound of the formula (I) (wherein m, p, $R^A$, $R^B$, $R^1$, $R^2$ and X are the same as defined above) can be prepared by reacting the compound of the formula (IV) (wherein m, p, $R^1$ and X are the same as defined above) with phosgene, diphosgene, triphosgene, 1,1-carbonyldiimidazole (CDI), or 1,1'-carbonyldi(1,2,4-triazole) (CDT) and then adding the compound of the formula (II) (wherein $R^A$, $R^B$ and $R^2$ are the same as defined above) to the reaction mixture.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N, N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 20° C. to 50° C. The reaction may be conducted for, usually, 30 minutes to 24 hours and preferably 1 to 10 hours.

[Method E]

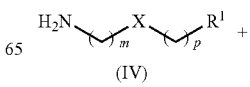

-continued

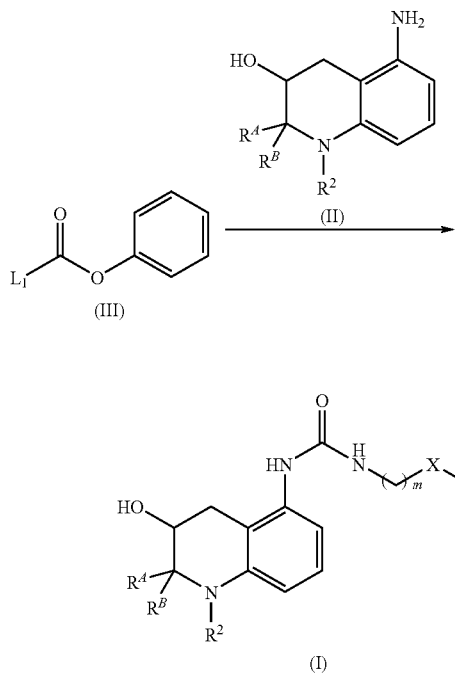

[Method F]

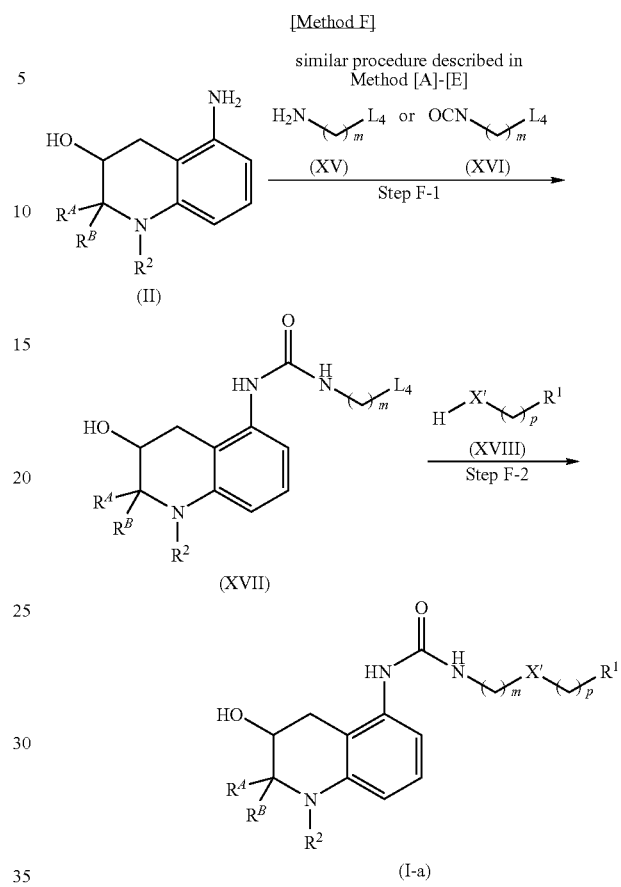

The compound of the formula (I) (wherein m, p, $R^A$, $R^B$, $R^1$, $R^2$ and X are the same as defined above) can be prepared by reacting the compound of the formula (IV) (wherein m, p, $R^1$ and X are the same as defined above) and the compound of the formula (III) (wherein $L_1$ is the same as defined above), and then adding the compound of the formula (II) (wherein $R^A$, $R^B$ and $R^2$ are the same as defined above) to the reaction mixture.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitrites such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 20° C. to 50° C. The reaction may be conducted for, usually, 30 minutes to 24 hours and preferably 1 to 10 hours.

The reaction can be advantageously carried out in the presence of a base including, for instance, organic amines such as pyridine, triethylamine and N,N-diisopropylethylamine, dimethylaniline, diethylaniline, 4-dimethylaminopyridine, and others.

The compound of the formula (I-a) (wherein m, p, $R^A$, $R^B$, $R^1$ and $R^2$ are the same as defined above; and X' is —O—, or $N(R^{10})$—) can be prepared by the following procedures.

In the Step F-1, the compound of the formula (XVII) (wherein m, $R^A$, $R^B$ and $R^2$ are the same as defined above and $L_4$ represents leaving group including, for instance, halogen atom such as chlorine, bromine, or iodine atom) can be prepared in a similar manner as described in Method [A], [B], [C], [D] or [E] for the preparation of the compound of the formula (I) by using a compound of the formula (XV) (wherein m and $L_4$ are the same as defined above) instead of the compound of the formula (IV), or using a compound of the formula (XVI) (wherein m and $L_4$ are the same as defined above) instead of the compound of the formula (V).

In the Step F-2, the compound of the formula (I-a) (wherein m, p, $R^A$, $R^B$, $R^1$, $R^2$ and X' are the same as defined above) can be prepared by reacting the compound of the formula (XVII) (wherein m, $L_4$, $R^A$, $R^B$ and $R^2$ are the same as defined above) and the compound of the formula (XVII) (wherein p, $R^1$ and X' are the same as defined above).

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-methylacetamide (DMAC) and N-methylpyrrolidone (NMP); ureas such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 50° C. The reaction may be conducted for, usually, 30 minutes to 24 hours and preferably 0.1 to 10 hours.

The reaction can be advantageously carried out in the presence of a base including, for instance, organic amines such as pyridine, triethylaamine and N,N-diisopropylethylamine, dimethylaniline, diethylaniline, 4-dimethylaminopyridine, and others.

The compound (XVIII), (XIX) and (XXI) are commercially available or can be prepared by the use of known techniques.

Compounds of the formula (II) are defined by compounds of the formula (IIa) and (IIb).

Preparation of compound of the formula (IIa)

The compound of the formula (IIa) (wherein $R^2$ is the same as defined above) can be prepared by the following procedures.

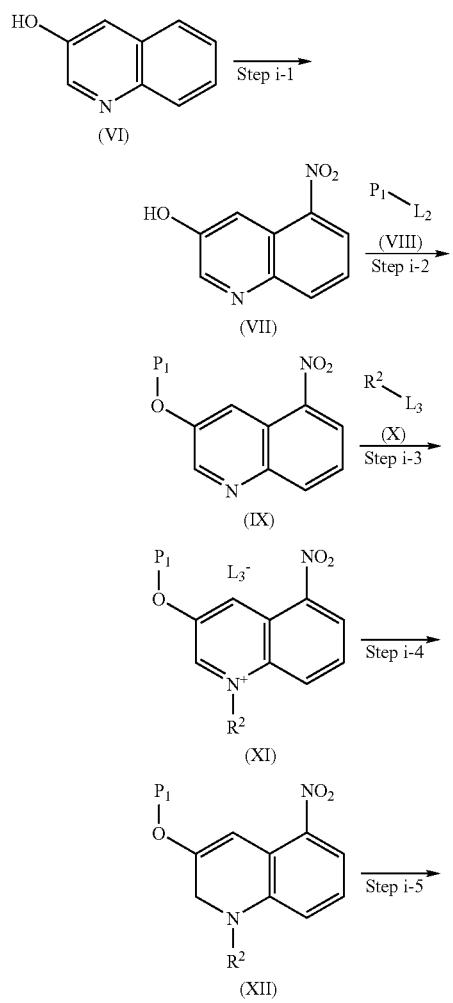

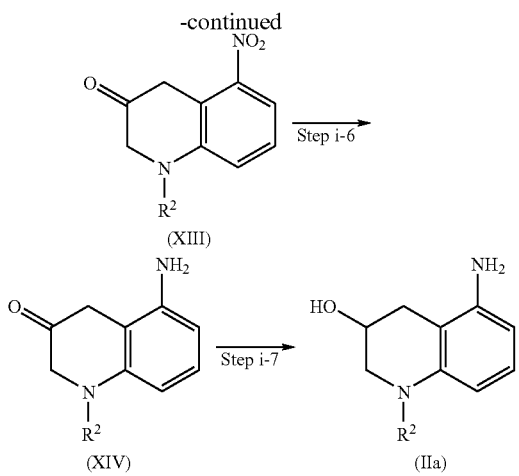

In the Step i-1, the compound of the formula (VII) can be prepared by the nitration of the compound of the formula (VI) using the agent including, for instance, nitric acid, potassium nitrate, and the like.

The reaction may be carried out in a solvent including, for instance, acid such as sulfuric acid; halogenated hydrocarbons such as dichloromethane, chloroform, 1,2-dichloroethane, and the like. Optionally, two or more of the solvents selected from the listed above can be mixed and used.

The reaction temperature can be optionally set depending on the compounds to be reacted. The reaction temperature is usually, but not limited to, about 0° C. to 100° C. The reaction may be conducted for, usually, 30 minutes to 24 hours and preferably 1 to 10 hours.

In the Step i-2, the compound of the formula (IX) (wherein $P_1$ represents alkyl such as methyl or ethyl and $L_2$ represents a leaving group including halogen atom such as chlorine, bromine, or iodine atom) can be prepared by the reaction of the compound of the formula (VII) with the compound of the formula (VIII) (wherein $L_2$ and $P_1$ are the same as defined above).

The reaction can be carried out in the presence of a base including, for instance, an alkali metal hydride such as sodium hydride or potassium hydride; alkali metal alkoxide such as sodium methoxide, sodium ethoxide and potassium tert-butoxide; alkali metal hydroxide such as sodium hydroxide and potassium hydroxide; alkali metal carbonates such as sodium carbonate and potassium carbonate; alkali metal hydrogen carbonates such as sodium hydrogen carbonate and potassium hydrogen carbonate; organic amines such as pyridine, triethylamine and N,N-diisopropylethylamine, dimethylaniline, diethylaniline, and others.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydro-carbons such as benzene, toluene and xylene; nitrites such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); nitrile such as acetonitrile and others. Optionally, two or more of the solvents selected from the listed above can be mixed and used.

The reaction temperature can be optionally set depending on the compounds to be reacted. The reaction temperature is usually, but not limited to, about 20° C. to 120° C. The reaction may be conducted for, usually, 30 minutes to 24 hours and preferably 1 to 10 hours.

In the Step i-3, the compound of the formula (XI) (wherein $P_1$ and $R^2$ are the same as defined above and $L_3$ represents a leaving group including halogen atom such as chlorine, bromine, or iodine atom; and arylsulfonyloxy such as p-toluenesulfonyloxy) can be prepared by the reaction of the compound of the formula (IX) (wherein $P_1$ is the same as defined above) with the compound of the formula (X) (wherein $L_3$ and $R^2$ are the same as defined above).

The reaction may be carried out in a solvent including, for instance, halogenated hydrocarbons such as dichloromethane, chloroform and 1,2-dichloroethane; ethers such as diethyl ether, iso-propyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); ketone such as acetone; nitrile such as acetonitrile and others. Optionally, two or more of the solvents selected from the listed above can be mixed and used.

The reaction temperature can be optionally set depending on the compounds to be reacted. The reaction temperature is usually, but not limited to, about 20° C. to 120° C. The reaction may be conducted for, usually, 30 minutes to 24 hours and preferably 1 to 10 hours.

In the Step i-4, the compound of the formula (XII) ((wherein $P_1$ and $R^2$ are the same as defined above) can be prepared by the reduction of the compound of the formula (XI) (wherein $L_3$, $P_1$ and $R^2$ are the same as defined above) using reducing agent such as sodium borohydride or sodium cyanoborohydride The reaction may be carried out in a solvent including, for instance, ethers such as diethyl ether, isopropyl ether, dioxane and tetrahydrofuran (THF) and 1,2-dimethoxyethane; alcohols such as methanol, ethanol, isopropanol, and others. Optionally, two or more of the solvents selected from the listed above can be mixed and used.

The reaction temperature can be optionally set depending on the compounds to be reacted. The reaction temperature is usually, but not limited to, about 20° C. to 50° C. The reaction may be conducted for, usually, 30 minutes to 24 hours and preferably 1 to 10 hours.

In the Step i-5, the compound of the formula (XIII) (wherein $R^2$ is the same as defined above) can be prepared by the reaction of the compound of the formula (XII) (wherein $P_1$ and $R^2$ are the same as defined above) with an acid such as hydrochloric acid.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2 dimethoxyethane; alcohols such as methanol, ethanol; water and others. Optionally, two or more of the solvents selected from the listed above can be mixed and used.

The reaction temperature can be optionally set depending on the compounds to be reacted. The reaction temperature is usually, but not limited to, about 20° C. to 100° C. The reaction may be conducted for, usually, 30 minutes to 24 hours and preferably 1 to 10 hours.

In the Step i-6, the compound of the formula (XIV) (wherein $R^2$ is the same as defined above) can be prepared by reducing nitro group of the compound of the formula (XIII) (wherein $R^2$ is the same as defined above) using an agent including, for instance, metals such as zinc and iron in the presence of acid including, for instance, hydrochloric acid and. acetic acid and stannous chloride, or by hydrogenation using a catalyst including, for instance, palladium on carbon and platinum on carbon.

The reaction can be carried out in a solvent including, for instance, ethers such as diethyl ether, isopropyl ether, dioxane, tetrahydrofuran (THF) and 1,2-dimethoxyethane, aromatic hydrocarbons such as benzene, toluene and xylene, alcohols such as methanol, ethanol, 1-propanol, isopropanol and tert-butanol, water and others.

The reaction temperature can be optionally set depending on the compounds to be reacted. The reaction temperature is usually, but not limited to, about 20° C. to 120° C. The reaction may be conducted for, usually, 30 minutes to 24 hours and preferably 1 to 10 hours.

In the Step i-7, the compound of the formula (IIa) (wherein $R^2$ is the same as defined above) can be prepared by reacting the compound of the formula (XIV) (wherein $R^2$ is the same as defined above) with a reducing agent such as sodium borohydride or lithium aluminum hydride.

The reaction may be carried out in a solvent including, for instance, ethers such as diethyl ether, isopropyl ether, dioxane and tetrahydrofuran (THF) and 1,2dimethoxyethane; alcohols such as methanol, ethanol, isopropanol, and others. Optionally, two or more of the solvents selected from the listed above can be mixed and used.

The reaction temperature can be optionally set depending on the compounds to be reacted. The reaction temperature is usually, but not limited to, about 20° C. to 50° C. The reaction may be conducted for, usually, 30 minutes to 24 hours and preferably 1 to 10 hours.

The compound (VI) is commercially available or can be prepared by the use of known techniques.

Preparation of Compound of the Formula (IIb)

The compound of the formula (IIb) (wherein $R^2$ is the same as defined above) can be prepared by the following procedures.

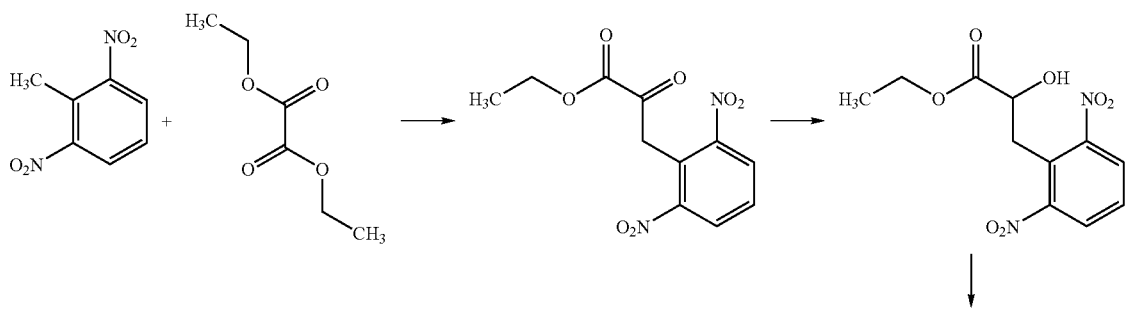

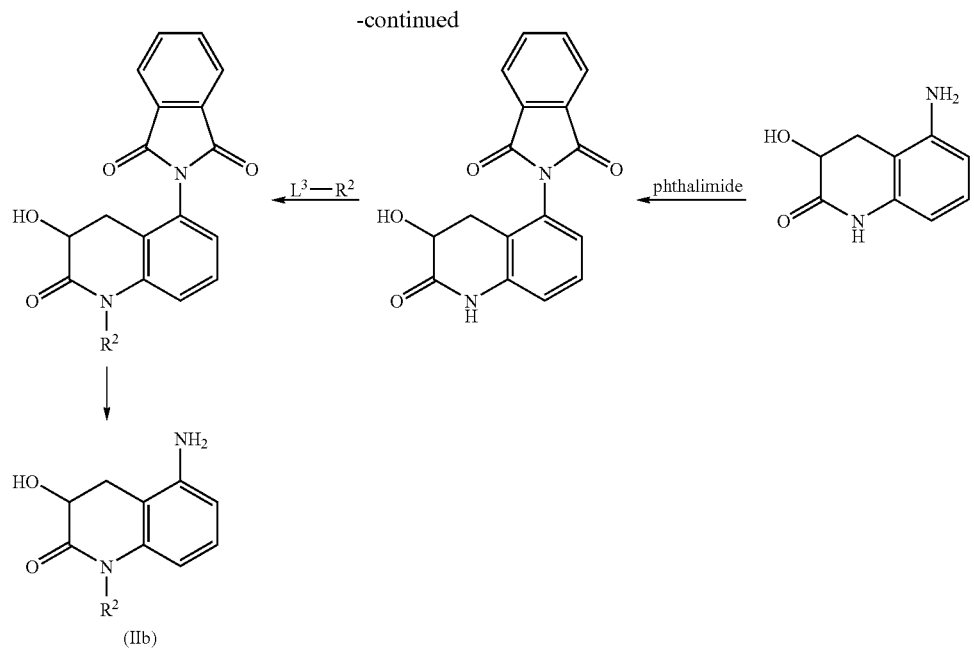

(IIb)

Reaction conditions for the preparation of (IIb) can be used in analogy to Masubuchi, Kazunao; Taniguchi, Mildo; Umeda, Isao; Hattori, Kazuo; Suda, Hitomi; Kohchi, Yasunori; Isshild, Yoshiaki; Sakai, Toshiya; Kohchi, Masami; Shirai, Michio; Okabe, Hisafimi; et al.; Bioorg. Med. Chem. Lett. 10; 13; 2000; 1459-1462.

When the compound shown by the formula (I) or a salt thereof has an asymmetric carbon in the structure, their optically active compounds and racemic mixtures are also included in the scope of the present invention.

Typical salts of the compound shown by the formula (I) include salts prepared by reaction of the compounds of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydriodic acid and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethyl-amine, tris (hydroxymethyl)aminomethane, and the like. Examples of inorganic bases include sodium hydroxide, potassium hydroxide, potassium carbonate, sodium carbonate, sodium bicarbonate, potassium bicarbonate, calcium hydroxide, calcium carbonate, and the like.

The compound of the present invention or a salt thereof, depending on its substituents, may be modified to form lower alkylesters or known other esters; and/or hydrates or other solvates. Those esters, hydrates, and solvates are included in the scope of the present invention.

The compound of the present invention may be administered in oral forms, such as, without limitation, normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well-known to those of ordinary skill in the pharmaceutical arts. The compounds of the present invention can be administered in intranasal form via topical use of suitable intranasal vehicles, or via transdermal routes, using transdermal delivery systems well-known to those of ordinary skilled in the art.

The dosage regimen with the use of the compounds of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds of the present invention are preferably formulated prior to administration together with one or more pharmaceutically-acceptable excipients. Excipients are inert substances such as, without limitation carriers, diluents, flavoring agents, sweeteners, lubricants, solubilizers, suspending agents, binders, tablet disintegrating agents and encapsulating material.

Yet another embodiment of the present invention is pharmaceutical formulation comprising a compound of the invention and one or more pharmaceutically-acceptable excipients that are compatible with the other ingredients of the formulation and not deleterious to the recipient thereof. Pharmaceutical formulations of the invention are prepared by combining a therapeutically effective amount of the compounds of the invention together with one or more pharmaceutically-acceptable excipients therefore. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely divided solid which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carriers, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the present invention, when used for the indicated effects, will range from about 0.01 mg/kg/day to about 100 mg/kg/day, preferably from 0.1 mg/kg/day to 30 mg/kg/day, and most preferably from about 0.5 mg/kg/day to about 10 mg/kg/day. In the case of parenteral administration, it has generally proven advantageous to administer quantities of about 0.001 to 100 mg /kg/day, preferably from 0.01 mg/kg/day to 1 mg/kg/day. The compounds of the present invention may be administered in a single daily dose, or the total daily dose may be administered in divided doses, two, three, or more times per day. Where delivery is via transdermal forms, of course, administration is continuous.

EXAMPLES

The present invention will be described as a form of examples, but they should by no means be construed as defining the metes and bounds of the present invention.

In the examples below, all quantitative data, if not stated otherwise, relate to percentages by weight.

Mass spectra were obtained using electrospray (ES) ionization techniques (micromass Platform LC). Melting points are uncorrected. Liquid Chromatography-Mass spectroscopy (LC-MS) data were recorded on a Micromass Platform LC with Shimadzu Phenomenex ODS column(4.6 mm□×30 mm) flushing a mixture of acetonitrile-water (9:1 to 1:9) at 1 ml/min of the flow rate. TLC was performed on a precoated silica gel plate (Merck silica gel 60 F-254). Silica gel (WAKO-gel C-200 (75-150 μm)) was used for all column chromatography separations. All chemicals were reagent grade and were purchased from Sigma-Aldrich, Wako pure chemical industries, Ltd., Great Britain, Tokyo kasei kogyo Co., Ltd., Nacalai tesque, Inc., Watanabe Chemical Ind. Ltd., Maybridge plc, Lancaster Synthesis Ltd., Merck KgaA, Germany, Kanto Chemical Co., Ltd.

$^1$H NMR spectra were recorded using either Bruker DRX-300 (300 MHz for $^1$H) spectrometer or Brucker 500 UltraShieled™ (500 MHz for 1 H). Chemical shifts are reported in parts per million (ppm) with tetrarethylsilane (TMS) as an internal standard at zero ppm. Coupling constant (J) are given in hertz and the abbreviations s, d, t, q, m, and br refer to singlet, doublet, triplet, quartet, multiplet, and broad, respectively. The mass determinations were carried out by MAT95 (Finnigan MAT).

All starting materials are commercially available or can be prepared using methods cited in the literature.

The effect of the present compounds was examined by the following assays and pharmacological tests.

[Measurement of Capsaicin-induced $Ca^{2+}$ Influx in the Human VR1-transfected CHO Cell Line] (Assay 1)

(1) Establishment of the Human VR1CHOluc9aeq Cell Line

Human vanilloid receptor (1VR1) cDNA was cloned from libraries of axotomized dorsal root ganglia (WO 00/29577). The cloned hVR1 cDNA was constructed with pcDNA3 vector and transfected into a CHOluc9aeq cell line. The cell line contains aequorin and CRE-luciferase *reporter* genes as read-out signals. The transfectants were cloned by limiting dilution in selection medium (DMEM/F12 medium (Gibco BRL) supplemented with 10% FCS, 1.4 mM Sodium pyruvate, 20 mM HEPES, 0.15% Sodium bicarbonate, 100 U/ml penicillin, 100 μg/ml streptomycin, 2 mM glutamine, non-essential amino acids and 2 mg/ml G418). $Ca^{2+}$ influx was examined in the capsaicin-stimulated clones. A high responder clone was selected and used for further experiments in the project. The human VR1CHOluc9aeq cells were maintained in the selection medium and passaged every 3-4 days at 1-2.5×10$^5$ cells/flask (75 mm$^2$).

(2) Measurement of $Ca^{2+}$ Influx using FDSS-3000

Human VR1-CHOluc9aeq cells were suspended in a culture medium which is the same as the selection medium except for G418 and seeded at a density of 1,000 cells per well into 384-well plates (black walled clear-base/Nalge Nunc International). Following the culture for 48 hrs the medium was changed to 2 µM Fluo-3 AM (Molecular Probes) and 0.02% Puronic F-127 in assay buffer (Hank's balanced salt solution (HBSS), 17 mM HEPES (pH 7.4), 1 mM Probenecid, 0.1% BSA) and the cells were incubated for 60 min at 25° C. After washing twice with assay buffer the cells were incubated with a test compound or vehicle for 20 min at 25° C. Mobilization of cytoplasmic $Ca^{2+}$ was measured by FDSS-3000 ($\lambda_{ex}$=488 nm, $\lambda_{em}$=540 nm/Hamamatsu Photonics) for 60 sec after the stimulation with 10 nM capsaicin. Integral R was calculated and compared with controls.

[Measurement of the Capsaicin-induced $Ca^{2+}$ Influx in Primary Cultured Rat Dorsal Root Ganglia Neurons] (Assay 2)

(1) Preparation of Rat Dorsal Root Ganglia Neurons

New born Wister rats (5-11 days) were sacrificed and dorsal root ganglia (DRG) was removed. DRG was incubated with 0.1% trypsin (Gibco BRL) in PBS(-) (Gibco BRL) for 30 min at 37° C., then a half volume of fetal calf serum (FCS) was added and the cells were spun down. The DRG neuron cells were resuspended in Ham F12/5% FCS/5% horse serum (Gibco BRL) and dispersed by repeated pipetting and passing through 70 µm mesh (Falcon). The culture plate was incubated for 3 hours at 37° C. to remove contaminating Schwann cells. Non-adherent cells were recovered and further cultured in laminin-coated 384 well plates (Nunc) at $1\times10^4$ cells/50 µl/well for 2 days in the presence of 50 ng/ml recombinant rat NGF (Sigma) and 50 µM 5-fluorodeoxyuridine (Sigma).

(2) $Ca^{2+}$ Mobilization Assay

DRG neuron cells were washed twice with HBSS supplemented with 17 mM HEPES (pH 7.4) and 0.1% BSA. After incubating with 2 µM fluo-3 AM (Molecular Probe), 0.02% PF127 (Gibco BRL) and 1 mM probenecid (Sigma) for 40 min at 37° C., cells were washed 3 times. The cells were incubated with VR1 antagonists or vehicle (dimethylsulfoxide) and then with 1 µM capsaicin in FDSS-6000 ($\lambda_{ex}$=480 nm, $\mu_{em}$=520nm/Hamamatsu Photonics). The fluorescence changes at 480 nm were monitored for 2.5 min. Integral R was calculated and compared with controls.

[Organ Bath Assay to Measure the Capsaicin-induced Bladder Contraction] (Assay 3)

Male Wister rats (10 week old) were anesthetized with ether and sacrificed by dislocating the necks. The whole urinary bladder was excised and placed in oxygenated Modified Krebs-Henseleit solution (pH 7.4) of the following composition (112 mM NaCl, 5.9 mM KCl, 1.2 mM $MgCl_2$, 1.2 mM $NaH_2PO_4$, 2 mM $CaCl_2$, 2.5 mM $NaHCO_3$, 12 mM glucose). Contractile responses of the urinary bladder were studied as described previously [Maggi C A et al: Br. J. Pharmacol. 108: 801-805, 1993]. Isometric tension was recorded under a load of 1 g using longitudinal strips of rat detrusor muscle. Bladder strips were equilibrated for 60 min before each stimulation. Contractile response to 80 mM KCl was determined at 15 min intervals until reproducible responses were obtained. The response to KCl was used as an internal standard to evaluate the maximal response to capsaicin. The effects of the compounds were investigated by incubating the strips with compounds for 30 min prior to the stimulation with 1 µM capsaicin (vehicle: 80% saline, 10% EtOH, and 10% Tween 80). One of the preparations made from the same animal was served as a control while the others were used for evaluating compounds. Ratio of each capsaicin-induced contraction to the internal standard (i.e. KCl-induced contraction) was calculated and the effects of the test compounds on the capsaicin-induced contraction were evaluated.

[Measurement of $Ca^{2+}$ Influx in the Human P2X1-transfected CHO Cell Line]

(1) Preparation of the Human P2X1-transfected CHOluc9aeq Cell Line

Human P2X1-transfected CHOluc9aeq cell line was established and maintained in Dulbecco's modified Eagle's medium (DMEM/F12) supplemented with 7.5% FCS, 20 mM HEPES-KOH (pH 7.4), 1.4 mM sodium pyruvate, 100 U/ml penicillin, 100 µg/ml streptomycin, 2 mM glutamine (Gibco BRL) and 0.5 Units/ml apyrase (grade I, Sigma). The suspended cells were seeded in each well of 384-well optical bottom black plates (Nalge Nunc International) at $3\times10^3/50$ µl/well. The cells were cultured for following 48 hrs to adhere to the plates.

(2) Measurement of the intracellular $Ca^{2+}$ levels

P2X1 receptor agonist-mediated increases in cytosolic $Ca^{2+}$ levels were measured using a fluorescent $Ca^{2+}$ chelating dye, Fluo-3 AM (Molecular Probes). The plate-attached cells were washed twice with washing buffer (HBSS, 17 mM HEPES-KOH (pH 7.4), 0.1% BSA and 0.5 units/ml apyrase), and incubated in 40 µl of loading buffer (1 µM Fluo-3 AM, 1 mM probenecid, 1 µM cyclosporin A, 0.01% pluronic (Molecular Probes) in washing buffer) for 1 hour in a dark place. The plates were washed twice with 40 µl washing buffer and 35 µl of washing buffer were added in each well with 5 µl of test compounds or 2',3'-o-(2,4,6-trinitrophenyl) adenosine 5'-triphpsphate (Molecular Probes) as a reference. After further incubation for 10 minutes in dark 200 nM α, β-methylene ATP agonist was added to initiate the $Ca^{2+}$ mobilization. Fluorescence intensity was measured by FDSS-6000 ($\lambda_{ex}$=410 nm, $\lambda_{em}$=510 nm/Hamamatsu Photonics) at 250 msec intervals. Integral ratios were calculated from the data and compared with that of a control.

[Measurement of Capsaicin-induced Bladder Contraction in Anesthetized Rats] (Assay 4)

(1) Animals

Female Sprague-Dawley rats (200-250 g/Charles River Japan) were used.

(2) Catheter Implantation

Rats were anesthetized by intraperitoneal administration of urethane (Sigma) at 1.2 g/kg. The abdomen was opened through a midline incision, and a polyethylene catheter (BECTON DICKINSON, PE50) was implanted into the bladder through the dome. In parallel, the inguinal region was incised, and a polyethylene catheter (Hibiki, size 5) filled with 2 IU / ml of heparin (Novo Heparin, Aventis Pharma) in saline (Otsuka) was inserted into a common iliac artery.

(3) Cystometric investigation

The bladder catheter was connected via T-tube to a pressure transducer (Viggo-Spectramed Pte Ltd, DT-XXAD) and a microinjection pump (TERUMO). Saline was infused at room temperature into the bladder at a rate of 2.4 ml/hr. Intravesical pressure was recorded continuously on a chart pen recorder (Yokogawa). At least three reproducible micturition cycles, corresponding to a 20-minute period, were recorded before a test compound administration and used as baseline values.

(4) Administration of Test Compounds and Stimulation of Bladder with Capsaicin

The saline infusion was stopped before administrating compounds. A testing compound dissolved in the mixture of ethanol, Tween 80 (ICN Biomedicals Inc.) and saline (1:1:8, v/v/v) was administered intraarterially at 10 mg/kg. 2 min after the administration of the compound 10 μg of capsaicin (Nacalai Tesque) dissolved in ethanol was administered intraarterially.

(5) Analysis of Cystometry Parameters

Relative increases in the capsaicin-induced intravesical pressure were analyzed from the cystometry data. The capsaicin-induced bladder pressures were compared with the maximum bladder pressure during micturition without the capsaicin stimulation. The testing compounds-mediated inhibition of the increased bladder pressures was evaluated using Student s t-test. A probability level less than 5% was accepted as significant difference.

[Measurement of Over Active Bladder in Anesthetized Cystitis Rats] (Assay 5)

(1) Animals

Female Sprague-Dawley rats (180~250 g/Charles River Japan) were used. Cyclo-phosphatidic (CUP) dissolved in saline was administered intraperitoneal at 150 mg/kg 48 hours before experiment.

(2) Catheter Implantation

Rats were anesthetized by intraperitoneal administration of urethane (Sigma) at 1.25 g/kg. The abdomen was opened through a midline incision, and a polyethylene catheter (BECTON DICKINSON, PE50) was implanted into the bladder through the dome. In parallel, the inguinal region was incised, and a polyethylene catheter (BECTON DICKINSON, PE50) filled with saline (Otsuka) was inserted into a femoral vein. After the bladder was emptied, the rats were left for 1 hour for recovery from the operation.

(3) Cystometric Investigation

The bladder catheter was connected via T-tube to a pressure transducer (Viggo-Spectramed Pte Ltd, DT-XXAD) and a microinjection pump (TERUMO). Saline was infused at room temperature into the bladder at a rate of 3.6 ml/hr for 20 min. Intravesical pressure was recorded continuously on a chart pen recorder (Yokogawa). At least three reproducible micturition cycles, corresponding to a 20-minute period, were recorded before a test compound administration.

(4) Administration of Test Compounds

A testing compound dissolved in the mixture of ethanol, Tween 80 (ICN Biomedicals Inc.) and saline (1:1:8, v/v/v) was administered intravenously at 0.05 mg/kg, 0.5 mg/kg or 5 mg/kg. 3 min after the administration of the compound, saline (Nacalai Tesque) was infused at room temperature into the bladder at a rate of 3.6 ml/hr.

(5) Analysis of Cystometry Parameters

The cystometry parameters were analyzed as described previously [Lecce A et al: Eur. J. Pharmacol. 259: 129-135, 1994]. The micturition frequency calculated from micturition interval and the bladder capacity calculated from a volume of infused saline until the first micturition were analyzed from the cystometry data. The testing compounds-mediated inhibition of the frequency and the testing compounds-mediated increase of bladder capacity were evaluated using unpaired Student s t-test. A probability levels less than 5% was accepted as significant difference. Data were analyzed as the mean±SEM from 4-7 rats.

[Measurement of Acute Pain]

Acute pain is measured on a hot plate mainly in rats. Two variants of hot plate testing are used: In the classical variant animals are put on a hot surface (52 to 56° C.) and the latency time is measured until the animals show nociceptive behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t., i.c.v., s.c., intradermal, transdermal) prior to pain testing.

[Measurement of Persistent Pain]

Persistent pain is measured with the formalin or capsaicin test, mainly in rats. A solution of 1 to 5% formalin or 10 to 100 μg capsaicin is injected into one hind paw of the experimental animal. After formalin or capsaicin application the animals show nociceptive reactions like flinching, licking and biting of the affected paw. The number of nociceptive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

[Measurement of Neuropathic Pain]

Neuropathic pain is induced by different variants of unilateral sciatic nerve injury mainly in rats. The operation is performed under anesthesia. The first variant of sciatic nerve injury is produced by placing loosely constrictive ligatures around the common sciatic nerve (Bennett and Xie, Pain 33 (1988): 87-107). The second variant is the tight ligation of about the half of the diameter of the common sciatic nerve (Seltzer et al., Pain 43 (1990): 205-218). In the next variant, a group of models is used in which tight ligations or transections are made of either the L5 and L6 spinal nerves, or the L5 spinal nerve only (KIM S H; CHUNG J M, AN EXPERIMENTAL-MODEL FOR PERIPHERAL NEUROPATHY PRODUCED BY SEGMENTAL SPINAL NERVE LIGATION IN THE RA, PAIN 50 (3) (1992): 355-363). The fourth variant involves an axotomy of two of the three terminal branches of the sciatic nerve (tibial and common peroneal nerves) leaving the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynia, as well as a thermal hyperalgesia. Mechanical allodynia is measured by means of a pressure transducer (electronic von Frey Anesthesiometer, IITC Inc.—Life Science Instruments, Woodland Hills, Calif., USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10° C. where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadian rhythms in activity (Suijo and Arndt, Universität zu Köln, Cologne, Germany), and by scoring differences in gait (foot print patterns; FOOT- PRINTS program, Klapdor et al., 1997. A low cost method to analyse footprint patterns. J. Neurosci. Methods 75, 49-54).

Compounds are tested against sham operated and vehicle treated control groups. Substance application is performed at different time points via different application routes (i.v., i.p., p.o., i.t., i.c.v., s.c., intradermal, transdermal) prior to pain testing.

[Measurement of Inflammatory Pain]

Inflammatory pain is induced mainly in rats by injection of 0.75 mg carrageenan or complete Freund's adjuvant into one hind paw. The animals develop an edema with mechanical allodynia as well as thermal hyperalgesia. Mechanical allodynia is measured by means of a pressure transducer (electronic von Frey Anesthesiometer, IITC Inc.—Life Science Instruments, Woodland Hills, Calif., USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hind paws sectioned and weighed. The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.c.v., s.c., intradermal, transdermal) prior to pain testing.

[Measurement of Diabetic Neuropathic Pain]

Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.—Life Science Instruments, Woodland Hills, Calif., USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

Results in capsaicin-induced $Ca^{2+}$ influx assay in the human VR1-transfected CHO cell line (Assay 1) are shown in Examples and tables of the Examples below. For practical reasons, the compounds are grouped in four classes based on activity as follows:

$IC_{50}=A(<or=)0.1 \mu M<B(<or=)0.5 \mu M<C(<or=)1 \mu M<D$

The compounds of the present invention also show excellent selectivity, and strong activity in other assays 2-5 and assays for pain described above.

Preparing method of compounds

[Starting compound A]

5-amino-1-methyl-1,2,3,4-tetrahydroquinolin-3-ol

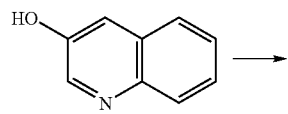

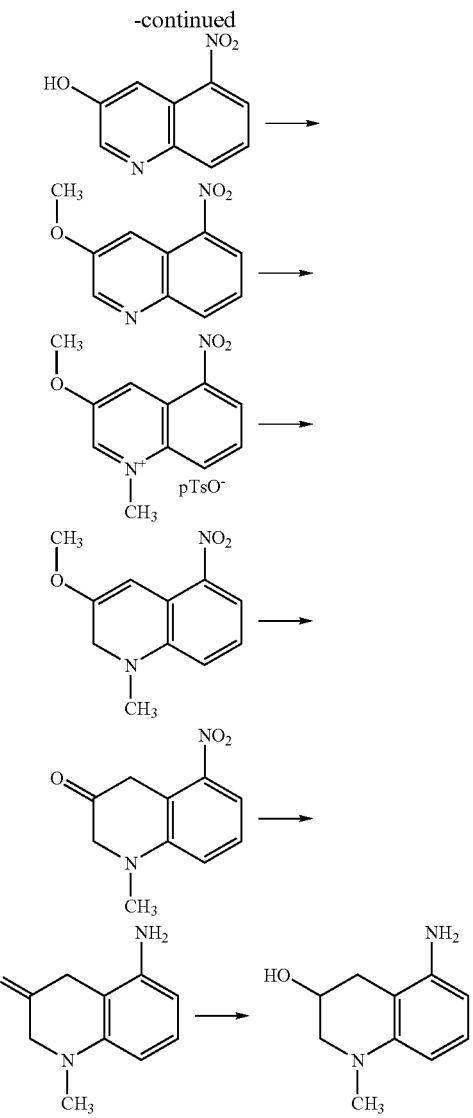

To a solution of concentrated sulfic acid is added concentrated nitric acid dropwise at −30° C. Quinolin-3-ol is added to the mixture at −30° C., and then stirred at 30° C. for 2 hours. After cooled to ambient temperature, the mixture is poured into water and then neutralized with aqueous 4N sodium hydroxide solution. After extracted with ethyl acetate, the organic layer is dried, filtered and concentrated under reduced pressure. The residue is purified by silica gel column chromatography to provide 5-nitroquinolin-3-ol.

To a solution of 5-nitroquinolin-3-ol in DMF is added sodium hydride at 0° C. Then, methyl iodide is added and the mixture is stirred for 2 h. Water is added and the mixture is extracted with ethyl acetate. The organic layer is dried, filtered and concentrated under reduced pressure to give 3-methoxy-5-nitroquinoline.

A mixture of 3-methoxy-5-nitroquinoline and methyl 4-methylbenzenesulfonate in acetonitrile is refluxed. After cooling, the precipitate is collected by filtration to provide 3-methoxy-1-methyl-5-nitroquinolinium 4-methylbenzenesulfonate.

To a solution of 3-methoxy-1-methyl-5-nitroquinolinium 4-methylbenzenesulfonate in methanol is added sodium borohydride at room temperature. The mixture is stirred at room temperature for 2 h and water is added. Water is added and the mixture is extracted with ethyl acetate. The organic layer is dried, filtered and concentrated under reduced pressure to give 3-methoxy-1-methyl-5-nitro-1,2-dihydroquinoline.

To a solution of 3-methoxy-1-methyl-5-nitro-1,2-4-hydroquinoline in tetrahydrofuran is added solution of aqueous 2N HCl, and stirred at 40° C. for 1 hour. The mixture is neutralized with sodium bicarbonate, and the mixture is. extracted with ethyl acetate. The organic layer is washed with water, dried, filtered, and concentrated under reduced pressure to afford 1-methyl-5-nitro-1,4-dihydroquinolin-3(2H)-one.

A mixture of 1-methyl-5-nitro-1,4-dihydroquinolin-3(2H)-one and catalytic amount of palladium on carbon in methanol is stirred under hydrogen for 3 hours. The resulting mixture is filtered through a pad of celite, and the filtrate is concentrated under reduced pressure to afford 5-amino-1-methyl-1,4-dihydroquinolin-3(2H)-one To a solution 5-anlino-1-methyl-1,4-dihydroquinolin-3(2H)-one in methanol is added sodium borohydride at 0° C., and the mixture is stirred for 1 hour. The mixture is poured into water, and the mixture is extracted with ethyl acetate. The organic layer is dried, filtered, and concentrated under reduced pressure to afford 5-amino-1-methyl-1,2,3,4-tetrahydroquinolin-3-ol.

Example 1-1

N-[4-chloro-3-(trifluoromethyl)phenyl]-N'-(3-hydroxy-1-methyl-1,2,3,4tetrahydroquinolin-5-yl)urea

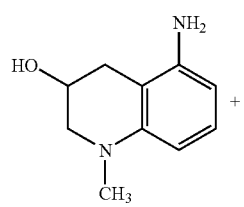

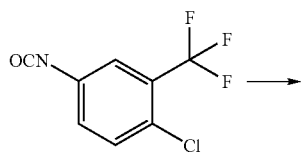

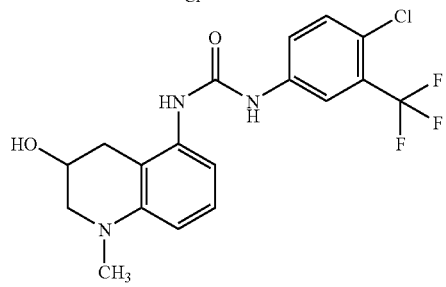

A mixture of 5-amino-1-methyl-1,2,3,4-tetrahydroquinolin-3-ol and 4-chloro-3-trifluoromethyl-phenyl isocyanate in tetrahydrofuran is stirred at 50° C. for 5 hours. After removing the solvent, the resulting residue is purified by silica gel column chromatography to provide N-[4-chloro-3-(trifluoromethyl)phenyl]-N'-(3-hydroxy-1-methyl-1,2,3,4-tetrahydroquinolin-5-yl)urea.

In a similar manner as described in Example 1-1, compounds shown below are synthesized.

| Example | m | p | —X— | —R |
|---------|---|---|-----|----|
| 1-2 | 0 | 1 | bond | 4-chlorophenyl |
| 1-3 | 1 | 1 | bond | 3-(trifluoromethyl)phenyl |
| 1-4 | 0 | 1 | bond | 3-(ethoxycarbonyl)phenyl |
| 1-5 | 0 | 2 | —O— | phenyl |
| 1-6 | 0 | 2 | —O— | 4-bromophenyl |
| 1-7 | 0 | 0 | —NH— | 2-chlorophenyl |
| 1-8 | 0 | 0 | —NH— | cyclohexyl |

Structure (Examples 2-x): N-methyl-3-hydroxy-1,2,3,4-tetrahydroquinolin-5-yl urea with –NH–C(=O)–NH–(CH₂)ₘ–X–(CH₂)ₚ–R¹

| Example | m | p | —X— | —R |
|---|---|---|---|---|
| 2-1 | 0 | 1 | bond | 3-(trifluoromethyl)phenyl |
| 2-2 | 0 | 1 | bond | cyclohexyl |
| 2-3 | 0 | 1 | —O— | 4-chlorophenyl |
| 2-4 | 0 | 0 | —O— | 3-(ethoxycarbonyl)phenyl |
| 2-5 | 0 | 0 | —NH— | 3-methoxyphenyl |
| 2-6 | 1 | 0 | bond | 4-bromophenyl |
| 2-7 | 1 | 1 | bond | cyclohexyl |
| 2-8 | 1 | 1 | bond | 2-naphthyl |

Structure (Examples 3-x): 3-hydroxy-1,2,3,4-tetrahydroquinolin-5-yl urea with –NH–C(=O)–NH–(CH₂)ₘ–X–(CH₂)ₚ–R¹

| Example | m | p | —X— | —R |
|---|---|---|---|---|
| 3-1 | 1 | 0 | bond | 3-methyl-2-(trifluoromethyl)-6-(piperidin-1-yl)phenyl |
| 3-2 | 2 | 0 | bond | cyclohexyl |
| 3-3 | 0 | 0 | —O— | 4-biphenyl |
| 3-4 | 0 | 0 | —O— | 3-(ethoxycarbonyl)phenyl |
| 3-5 | 0 | 0 | —NH— | 3-methoxyphenyl |
| 3-6 | 1 | 1 | bond | 2-naphthyl |
| 3-7 | 1 | 1 | bond | cyclohexyl |

[Staring Compound B]

Ethyl 3-(2,6-dinitrophenyl)-2-oxopropanoate

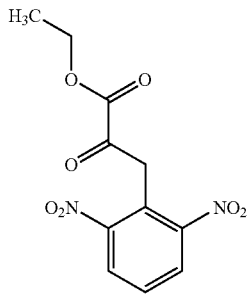

2,6-Dinitrotoluene (10.0 g, 54.9 mmol) and oxalic acid diethylester (16.1 g, 110 mmol) are dissolved in ethanol (100 ml). Sodium ethylate (apx 2.5 N in ethanol, 54.9 mmol) is added, the mixture is stirred at 40° C. for 2 h. The solution is cooled to room temperature, adjusted to pH=3-4 with 2N hydrochloric acid, the solvent is evaporated in vacuo, the residue is partitioned between ethyl acetate and water, the organic layer is washed with water twice, dried over magnesium sulfate, filtered and evaporated. The crude product is purified with column chromatography on silica gel (eluent: cyclohexane/ethyl acetate, 2:1). Yield: 3.15 g (20%), mixture of keto/enol tautomers $^1$H-NMR (DMSO, 200 MHz): δ 10.1 (s, 0.55H), 8.38 (d, 0.9H), 8.27 (d, 1.1H), 7.92-7.71 (m, 1H), 6.59 (s, 0.55H), 4.69 (s, 0.9H), 4.40-4.20 (2q, 2H), 1.35-1.23 (2t, 3H). Molecular weight: 282 MS (DCI$^+$): 300 (M+NH$_4$)$^+$ Ethyl 3-(2,6dinitrophenyl)-2-hydroxypropanoate

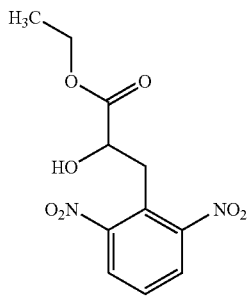

Ethyl 3-(2,6-dinitrophenyl)-2-oxopropanoate (3.16 g, 11.2 mmol) is dissolved in dry methanol and cooled to 0° C. Sodium borohydride (0.13 g, 3.36 mmol) is added at 0° C. and stirring continued at 0° C. for 30 min. The mixture is warmed to room temperature and stirred for another 15 min. Acetone (10 ml) is added and subsequently of saturated aq. NH$_4$Cl (5 ml) is added. The solvent is evaporated in vacuo, the remainder is dissolved in ethyl acetate and water, the organic layer is dried over magnesium sulfate, filtered and evaporated in vacuo. The crude product is purified with column chromatography on silica gel (eluent: cyclohexane/ethyl acetate, 1:1). Yield: 1.43 g (44%)

$^1$H-NMR (DMSO, 300 MHz): δ 8.2 (d, 2H), 7.75 (t, 2H), 5.88 (d, 1H), 4.20 (ddd, 1H), 4.08 (q, 2H), 3.45 (dd, 1H), 3.30 (dd, 1H), 1.17 (t, 3H). Molecular weight: 284 MS (DCI$^+$): 301.9 (M+NH$_4$)$^+$ 5-Amino-3-hydroxy-3,4-dihydroquinolin-2(1H)-one

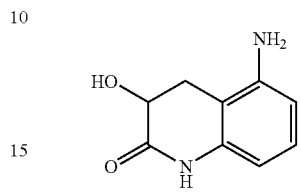

Ethyl 3-2,6-dinitrophenyl)-2-hydroxypropanoate (1.44 g, 5.05 mmol) is dissolved in ethanol, Pd/10% C (53 mg) is added and the mixture is stirred over night under a H$_2$ atmosphere (1 bar). The reaction mixture is filtered over celite and rinsed with ethanol. The solvent is evaporated in vacuo, the crude product is purified using vacuum-flash chromatography on silica (eluent: ethyl acetate). The isolated product fraction is stirred with diethyl ether, the product is filtered and dried in vacuo. Yield: 352 mg (37%).

$^1$H-NMR (DMSO, 300 MHz): δ 9.85 (s, 1H), 6.8 (t, 1H), 6.26 (d, 1H), 6.09 (d, 1H), 5.23 (s, 1H), 5.00 (s, 2H), 4.05 (dd, 1H), 3.01 (dd, 1H), 2.40 (dd, 1H). Molecular weight: 178 MS (ESI$^+$): 179 (M+H)$^+$

[Starting Compound C]

5-Amino-1,2,3,4-tetrahydroquinolin-3-ol

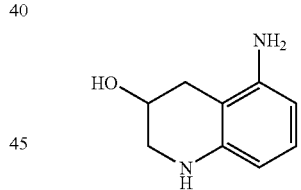

5-Amino-3-hydroxy-3,4-dihydroquinolin-2(1H)-one (300 mg, 1.68 mmol) is dissolved in THF (10 ml) and slowly added to a refluxing mixture of LiAlH$_4$ (319 mg, 8.42 mmol) in 8 ml THF under an argon atmosphere. After 30 min refluxing the mixture is cooled to room temperature, ethyl acetate (10 ml) is added cautiously, thereafter water is added slowly and cautiously until a light grey precipitate formed. The solvent is collected and the precipitate is washed several times with ethyl acetate, the combined organic extracts are washed with water, dried over magnesium sulfate, filtered and evaporated to dryness. The crude material is purified by column chromatography (eluent: ethyl acetate). Yield: 182 mg (65%/).

$^1$H-NMR (DMSO, 300 MHz): δ 6.54 (t, 1H), 5.86 (d, 1H), 5.75 (d, 1H), 5.21 (d br, 1H), 4.78 (d, 1H), 4.45 (s, 2H), 3.9-3.77 (m, 1H), 3.18-3.07 (m, 1H), 2.75 (dd, 1H), 2.60 (ddd, 1H), 2.13 (dd, 1H). Molecular weight: 164 MS (DCI$^+$): 165 (M+H)$^+$

Example 4-1

N-(3-Hydroxy-2-oxo-1,2,3,4-tetrahydroquinolin-5-yl)-N'-[4-(trifluoromethyl)benzyl]urea

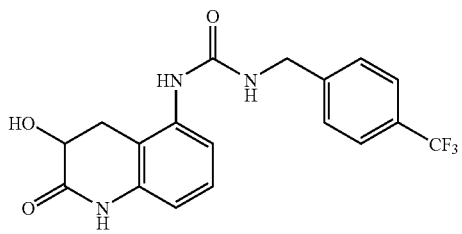

5-Amino-3-hydroxy-3,4-dihydroquinolin-2(1H)-one (300 mg, 1.68 mmol) is dissolved in ethyl acetate and cooled to 0° C. 4-Trifluoromethylbenzylisocyanate (339 mg, 1.68 mmol) is added slowly with stirring. The reaction mixture is stirred for 1 h at room temperature. The insoluble product is filtered and dried in vacuo. Yield: 103 mg (16%).

$^1$H-NMR (DMSO, 300 MHz): δ 10.08 (s, 1H), 8.01 (s, 1H), 7.70 (d, 2H), 7.52 (d, 2H), 7.41 (d, 1H), 7.12-6.95 (m, 2H), 6.54 (d, 1H), 5.42 (d, 1H), 4.40 (d, 1H), 4.18-4.02 (m, 1H), 3.09 (dd, 1H), 2.61 (dd, 1H). Molecular weight: 379 MS (ESI$^+$): 380 (M+H)$^+$

Example 4-2

N-(3-Hydroxy-1,2,3,4-tetrahydroquinolin-5-yl)-N'-[4-(trifluoromethyl)benzyl]urea

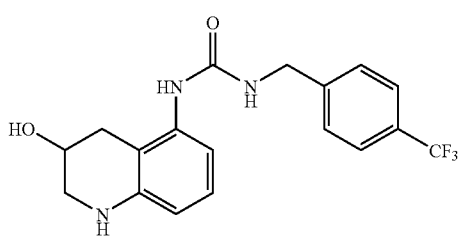

5-Amino-1,2,3,4-tetrahydroquinolin-3-ol (36.4 mg, 0.22 mmol) is dissolved in dichloromethane and cooled to −20° C. 4-Trifluoromethylbenzylisocyanate (44.6 mg, 0.22 mmol) is added and the reaction mixture is warmed to room temperature over 4 h. The organic layer is diluted with dichloromethane, washed with aq. NH$_4$Cl and water. The organic phase is dried over magnesium sulfate, filtered and evaporated to dryness. The crude product consists of a mixture of regioisomers and is separated using preparative HPLC with an acetonitrile/water gradient.

$^1$H-NMR (DMSO, 500 MHz): δ 7.71 (d, 2H), 7.60 (s, 1H), 7.51 (d, 2H), 7.04 (t, 1H), 6.97 (d, 1h), 6.75 (t, 1H), 6.15 (d, 1H), 5.58 (s, 1H), 4.95 (d, 1H), 4.37 (d, 2H), 3.92-3.83 (m, 1H), 3.17 (d, 1H), 2.81 (t, 1H), 2.73 (dd, 1H), 2.30 (dd, 1H). Molecular weight: 365 MS (ESI$^+$): 366.1 (M+H)$^+$.

The invention claimed is:

1. A urea derivative of the formula (I), its tautomeric or stereoisomeric form, or a salt thereof:

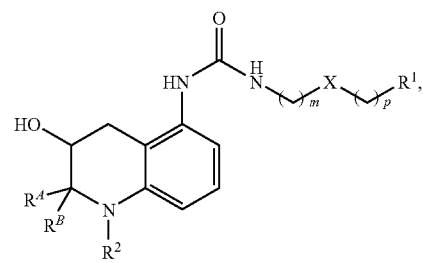

wherein m represents 0, 1, 2, or 3;

p represents 0, 1, 2, or 3;

—X— represents a bond, —O— or —N(R$^{10}$)— (wherein R$^{10}$ is hydrogen or C$_{1-6}$ alkyl);

with the proviso that when m is 0, —X— represents a bond,

R$^A$ and R$^B$ represent hydrogen, or

R$^A$ and R$^B$ together form a carbonyl-group with the carbon-atom to which they are connected, R$^1$ represents aryl or heteroaryl wherein said aryl and heteroaryl are optionally substituted with one or more substituents independently selected from the group consisting of halogen, nitro, hydroxy, carboxy, amino, C$_{1-6}$ alkylamino, di(C$_{1-6}$ alkyl)amino, C$_{3-8}$ cycloalkylamino, C$_{1-6}$ alkoxycarbonyl, phenyl (which phenyl is optionally substituted by halogen, nitro, hydroxy, carboxy, amino, C$_{1-6}$ alkylamino, di(C$_{1-6}$ alkyl)amino, C$_{3-8}$ cycloalkylamino, or C$_{1-6}$ alkoxycarbonyl), benzyl (in which phenyl moiety is optionally substituted by halogen, nitro, hydroxy, carboxy, amino, C$_{1-6}$ alkylamino, di(C$_{1-6}$ alkyl)amino, C$_{3-8}$ cycloalkylamino, or C$_{1-6}$ alkoxycarbonyl), sulfonamide, C$_{1-6}$ alkanoyl, C$_{1-6}$ alkanoylamino, carbamoyl, C$_{1-6}$ alkylcarbamoyl, cyano, C$_{1-6}$ alkyl (which alkyl is optionally substituted by cyano, nitro, hydroxy, carboxy, amino, C$_{1-6}$ alkoxycarbonyl or mono-, di-, or tri-halogen), C$_{1-6}$ alkoxy (which alkoxy is optionally substituted by mono-, di-, or tri-halogen), phenoxy (in which phenyl moiety is optionally substituted by halogen, nitro, hydroxy, carboxy, amino, C$_{1-6}$ alkylamino, di(C$_{1-6}$ alkyl)amino, C$_{3-8}$ cycloalkylamino, or C$_{1-6}$ alkoxycarbonyl or C$_{1-6}$ alkyl), C$_{1-6}$ alkylthio (which alkylthio is optionally substituted by mono-, di-, or tri-halogen), C$_{3-8}$ cycloalkyl, and heterocycle; and R$^2$ represents C$_{1-6}$alkylcarbonyl, C$_{1-6}$alkylsulfonyl, hydrogen, hydroxy, aryl, heteroaryl, C$_{1-6}$alkyl, C$_{2-6}$alkenyl, C$_{2-6}$alkynyl, C$_{3-8}$cycloalkyl, arylsulfonyl, or heteroarylsulfonyl, wherein said alkyl, alkenyl or alkynyl are optionally substituted by mono-, di-, or tri-halogen, hydroxy, carboxyl, nitro, cyano, C$_{1-6}$alkoxy, C$_{1-6}$alkoxycarbonyl, C$_{3-8}$cycloalkyl, amino, N-(C$_{1-6}$alkyl)amino, N,N-di (C$_{1-6}$alkyl)amino, N-(aryl)amino, N-(heteroaryl) amino, carbamoyl, N-(C$_{1-6}$alkyl)aminocarbonyl, or N,N,-di(C$_{1-6}$alkyl)aminocarbonyl, and said cycloalkyl, aryl, heteroaryl, aryl moiety of said arylsulfonyl, or heteroaryl moiety of said heteroarylsulfonyl are optionally substituted by mono-, di-, or tri-halogen, hydroxy, carboxyl, cyano, nitro, ($C_{1-6}$alkoxy)carbonyl, $C_{3-8}$cycloalkyl, amino, N-($C_{1-6}$alkyl)amino, N,N-di($C_{1-6}$alkyl)amino, N-(aryl)amino, N-(heteroaryl)amino, carbamoyl, N-($C_{1-6}$alkyl)aminocarbonyl, N,N-di($C_{1-6}$alkyl)aminocarbonyl, $C_{1-6}$alkyl optionally substituted by mono-, di-, or tri-halogen, or $C_{1-6}$alkoxy optionally substituted by mono-, di-, or tri-halogen.

2. The urea derivative of formula (I), its tautomeric or stereoisomeric form, or a salt thereof as claimed in claim 1, wherein m represents 0, 1, 2, or 3;

p represents 0, 1, 2, or 3;

—X— represents a bond, —O— or —N($R^{10}$)— (wherein $R^{10}$ is hydrogen or $C_{1-6}$ alkyl);

with the proviso that when m is 0, —X— represents a bond, $R^A$ and $R^B$ represent hydrogen, $R^1$ represents aryl or heteroaryl wherein said aryl and heteroaryl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$alkylamino, di($C_{1-6}$alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle; and $R^2$ represents $C_{1-6}$alkylcarbonyl, $C_{1-6}$alkylsulfonyl, hydrogen, hydroxy, aryl, heteroaryl, $C_{1-6}$alkyl, $C_{2-6}$alkenyl, $C_{2-6}$alkynyl, $C_{3-8}$cycloalkyl, arylsulfonyl, or heteroarylsulfonyl, wherein said alkyl, alkenyl or alkynyl are optionally substituted by mono-, di-, or tri-halogen, hydroxy, carboxyl, nitro, cyano, $C_{1-6}$alkoxy, $C_{1-6}$alkoxycarbonyl, $C_{3-8}$cycloalkyl, amino, N-($C_{1-6}$alkyl)amino, N,N-di($C_{1-6}$alkyl)amino, N-(aryl)amino, N-(heteroaryl)amino, carbamoyl, N-($C_{1-6}$alkyl)aminocarbonyl, or N,N,-di-($C_{1-6}$alkyl)- aminocarbonyl, and said cycloalkyl, aryl, heteroaryl, aryl moiety of said arylsulfonyl, or heteroaryl moiety of said heteroarylsulfonyl are optionally substituted by mono-, di-, or tri-halogen, hydroxy, carboxyl, cyano, nitro, ($C_{1-6}$alkoxy)carbonyl, $C_{3-8}$cycloalkyl, amino, N-($C_{1-6}$alkyl)amino, N,N-di($C_{1-6}$-alkyl)amino, N-(aryl)amino, N-(heteroaryl)amino, carbamoyl, N-($C_{1-6}$-alkyl)aminocarbonyl, N,N-di-($C_{1-6}$-alkyl) aminocarbonyl, $C_{1-6}$alkyl optionally substituted by mono-, di-, or tri-halogen, or $C_{1-6}$alkoxy optionally substituted by mono-, di-, or tri-halogen.

3. The urea derivative of formula (I), its tautomeric or stereoisomeric form, or a salt thereof as claimed in claim 1, wherein m represents 0, 1, 2, or 3;

p represents 0, 1, 2, or 3;

—X— represents a bond, —O— or —N($R^{10}$)— (wherein $R^{10}$ is hydrogen or $C_{1-6}$ alkyl);

with the proviso that when m is 0, —X— represents a bond, $R^A$ and $R^B$ represent hydrogen, $R^1$ represents phenyl, naphthyl, pyridyl, or pyrimidyl, wherein said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle; and $R^2$ represents $C_{1-6}$alkylcarbonyl, $C_{1-6}$alkylsulfonyl, hydrogen, hydroxy, aryl, heteroaryl, $C_{1-6}$alkyl, $C_{2-6}$alkenyl, $C_{2-6}$alkynyl, $C_{3-8}$cycloalkyl, arylsulfonyl, or heteroarylsulfonyl, wherein said alkyl, alkenyl or alkynyl are optionally substituted by mono-, di-, or tri-halogen, hydroxy, carboxyl, nitro, cyano, $C_{1-6}$alkoxy, $C_{1-6}$alkoxycarbonyl, $C_{3-8}$cycloalkyl, amino, N-($C_{1-6}$alkyl)amino, N,N-di ($C_{1-6}$alkyl)amino, N-(aryl)amino, N-(heteroaryl) amino, carbamoyl, N-($C_{1-6}$alkyl)aminocarbonyl, or N,N,-di-($C_{1-6}$alkyl)aminocarbonyl, and said cycloalkyl, aryl, heteroaryl, aryl moiety of said arylsulfonyl, or heteroaryl moiety of said heteroarylsulfonyl are optionally substituted by mono-, di-, or tri-halogen, hydroxy, carboxyl, cyano, nitro, ($C_{1-6}$alkoxy)carbonyl, $C_{3-8}$cycloalkyl, amino, N-($C_{1-6}$alkyl)amino, N,N-di($C_{1-6}$alkyl)amino, N-(aryl)amino, N-(heteroaryl)amino, carbamoyl, N-($C_{1-6}$alkyl)aminocarbonyl, N,N-di($C_{1-6}$alkyl)aminocarbonyl, $C_{1-6}$alkyl optionally substituted by mono-, di-, or tri-halogen, or $C_{1-6}$alkoxy optionally substituted by mono-, di-, or tri-halogen.

4. The urea derivative of formula (I), its tautomeric or stereoisomeric form, or a salt thereof as claimed in claim 1, wherein m represents 0, 1, 2, or 3;

p represents 0, 1, 2, or 3;

—X— represents a bond, —O— or —N(R$^{10}$)— (wherein R$^{10}$ is hydrogen or C$_{1-6}$ alkyl);

with the proviso that when m is 0, —X— represents a bond,

R$^A$ and R$^B$ represent hydrogen,

R$^1$ represents phenyl, naphthyl, pyridyl, or pyrimidyl, wherein said phenyl, naphthyl, pyridyl and pyrimidyl are optionally substituted with one or more substituents independently selected from the group consisting of halogen, nitro, hydroxy, carboxy, amino, C$_{1-6}$ alkylamino, di(C$_{1-6}$ alkyl)amino, C$_{3-8}$ cycloalkylamino, C$_{1-6}$ alkoxycarbonyl, phenyl (which phenyl is optionally substituted by halogen, nitro, hydroxy, carboxy, amino, C$_{1-6}$alkylamino, di(C$_{1-6}$alkyl)amino, C$_{3-8}$ cycloalkylamino, or C$_{1-6}$ alkoxycarbonyl), benzyl (in which phenyl moiety is optionally substituted by halogen, nitro, hydroxy, carboxy, amino, C$_{1-6}$ alkylamino, di(C$_{1-6}$ alkyl)amino, C$_{3-8}$ cycloalkylamino, or C$_{1-6}$ alkoxycarbonyl), sulfonamide, C$_{1-6}$ alkanoyl, C$_{1-6}$ alkanoylamino, carbamoyl, C$_{1-6}$ alkylcarbamoyl, cyano, C$_{1-6}$ alkyl (which alkyl is optionally substituted by cyano, nitro, hydroxy, carboxy, amino, C$_{1-6}$ alkoxycarbonyl or mono-, di-, or tri-halogen), C$_{1-6}$ alkoxy (which alkoxy is optionally substituted by mono-, di-, or tri-halogen), phenoxy (in which phenyl moiety is optionally substituted by halogen, nitro, hydroxy, carboxy, amino, C$_{1-6}$ alkylamino, di(C$_{1-6}$ alkyl)amino, C$_{3-8}$ cycloalkylamino, or C$_{1-6}$ alkoxycarbonyl or C$_{1-6}$ alkyl), C$_{1-6}$ alkylthio (which alkylthio is optionally substituted by mono-, di-, or tri-halogen), C$_{3-8}$ cycloalkyl, and heterocycle; and R$^2$ represents C$_{1-6}$alkylcarbonyl, C$_{1-6}$alkylsulfonyl, hydrogen, hydroxy, phenyl, naphthyl, pyridyl, of pyrimidyl, C$_{1-6}$alkyl, C$_{2-6}$alkenyl, C$_{2-6}$alkynyl, C$_{3-8}$cycloalkyl, phenysulfonyl, pyrimidylsulfonyl, or pyridylsulfonyl, wherein said alkyl, alkenyl or alkynyl are optionally substituted by mono-, di-, or tri-halogen, hydroxy, carboxyl, nitro, cyano, C$_{1-6}$alkoxy, C$_{1-6}$alkoxycarbonyl, C$_{3-8}$cycloalkyl, amino, N-(C$_{1-6}$alkyl)amino, N,N-di(C$_{1-6}$alkyl)amino, N-(aryl)amino, N-(heteroaryl)amino, carbamoyl, N-(C$_{1-6}$alkyl)aminocarbonyl, or N,N,-di-(C$_{1-6}$alkyl)- aminocarbonyl, and said cycloalkyl, phenyl, naphthyl, pyridyl, pyrimidyl, phenyl moiety, pyridyl moiety or pyrimidyl moiety of said phenylsulfonyl, pyridylsulfonyl, pyrimidyl-sulfonyl are optionally substituted by mono-, di-, or tri-halogen, hydroxy, carboxyl, cyano, nitro, (C$_1$-alkoxy)carbonyl, C$_{3-8}$cycloalkyl, amino, N-(C$_{1-6}$-alkyl)amino, N,N-di(C$_{1-6}$alkyl)amino, N-(aryl)amino, N-(heteroaryl)amino, carbamoyl, N-(C$_{1-6}$alkyl)aminocarbonyl, N,N-di (C$_{1-6}$alkyl)-aminocarbonyl, C$_{1-6}$alkyl optionally substituted by mono-, di-, or tri-halogen, or C$_{1-6}$alkoxy optionally substituted by mono-, di-, or tri-halogen.

5. The urea derivative of formula (I), its tautomeric or stereoisomeric form, or a salt thereof as claimed in claim 1, wherein m represents 0, 1, 2, or 3;

p represents 0;

—X— represents a bond;

R$^A$ and R$^B$ represent hydrogen,

R$^1$ represents phenyl, naphthyl, pyridyl, or pyrimidyl, wherein said phenyl, naphthyl, pyridyl and pyrimidyl are optionally substituted with one or more substituents independently selected from the group consisting of halogen, nitro, hydroxy, carboxy, amino, C$_{1-6}$ alkylamino, di(C$_{1-6}$ alkyl)amino, C$_{3-8}$ cycloalkylamino, C$_{1-6}$ alkoxycarbonyl, phenyl (which phenyl is optionally substituted by halogen, nitro, hydroxy, carboxy, amino, C$_{1-6}$ alkylamino, di(C$_{1-6}$ alkyl)amino, C$_{3-8}$ cycloalkylamino, or C$_{1-6}$ alkoxycarbonyl), benzyl (in which phenyl moiety is optionally substituted by halogen, nitro, hydroxy, carboxy, amino, C$_{1-6}$ alkylamino, di(C$_{1-6}$ alkyl)amino, C$_{3-8}$ cycloalkylamino, or C$_{1-6}$ alkoxycarbonyl), sulfonamide, C$_{1-6}$ alkanoyl, C$_{1-6}$ alkanoylamino, carbamoyl, C$_{1-6}$ alkylcarbamoyl, cyano, C$_{1-6}$ alkyl (which alkyl is optionally substituted by cyano, nitro, hydroxy, carboxy, amino, C$_{1-6}$ alkoxycarbonyl or mono-, di-, or tri-halogen), C$_{1-6}$ alkoxy (which alkoxy is optionally substituted by mono-, di-, or tri-halogen), phenoxy (in which phenyl moiety is optionally substituted by halogen, nitro, hydroxy, carboxy, amino, C$_{1-6}$ alkylamino, di(C$_{1-6}$ alkyl)amino, C$_{3-8}$ cycloalkylamino, or C$_{1-6}$ alkoxycarbonyl or C$_{1-6}$ alkyl), C$_{1-6}$ alkylthio (which alkylthio is optionally substituted by mono-, di-, or tri-halogen), C$_{3-8}$ cycloalkyl, and heterocycle; and R$^2$ represents C$_{1-6}$alkylcarbonyl, C$_{1-6}$alkylsulfonyl, hydrogen, hydroxy, phenyl, naphthyl, pyridyl, of pyrimidyl, C$_{1-6}$alkyl, C$_{2-6}$alkenyl, C$_{2-6}$alkynyl, C$_{3-8}$cycloalkyl, phenylsulfonyl, pyrimidylsulfonyl, or pyridylsulfonyl, wherein said alkyl, alkenyl or alkynyl are optionally substituted by mono-, di-, or tri-halogen, hydroxy, carboxyl, nitro, cyano, C$_{1-6}$alkoxy, C$_{1-6}$alkoxycarbonyl, C$_{3-8}$cycloalkyl, amino, N-(C$_{1-6}$alkyl)amino, N,N-di(C$_{1-6}$alkyl)amino, N-(aryl)amino, N-(heteroaryl)amino, carbamoyl, N-(C$_{1-6}$alkyl)aminocarbonyl, or N,N,-di(C$_{1-6}$alkyl)aminocarbonyl, and said cycloalkyl, phenyl, naphthyl, pyridyl, pyrimidyl, phenyl moiety, pyridyl moiety or pyrimidyl moiety of said phenylsulfonyl, pyridylsulfonyl, pyrimidylsulfonyl are optionally substituted by mono-, di-, or tri-halogen, hydroxy, carboxyl, cyano, nitro, (C$_{1-6}$alkoxy)carbonyl, C$_{3-8}$cycloalkyl, amino, N-(C$_{1-6}$alkyl)amino, N,N-di(C$_{1-6}$alkyl)amino, N-(aryl)amino, N-(heteroaryl)amino, carbamoyl, N-(C$_{1-6}$alkyl)aminocarbonyl, N,N-di(C$_{1-6}$alkyl)aminocarbonyl, C$_{1-6}$alkyl optionally substituted by mono-, di-, or tri-halogen, or C$_{1-6}$alkoxy optionally substituted by mono-, di-, or tri-halogen.

6. The urea derivative of formula (I), its tautomeric or stereoisomeric form, or a salt thereof as claimed in claim 1, wherein m represents 1, 2, or 3;

p represents 0, 1, 2, or 3;

—X— represents a bond, —O— or —N(R$^{10}$)— (wherein R$^{10}$ is hydrogen or C$_{1-6}$ alkyl);

R$^A$ and R$^B$ represent hydrogen,

R$^1$ represents phenyl, naphthyl, pyridyl, or pyrimidyl, wherein said phenyl, naphthyl, pyridyl and pyrimidyl are optionally substituted with one or more substituents independently selected from the group consisting of halogen, nitro, hydroxy, carboxy, amino, C$_{1-6}$alkylamino, di(C$_{1-6}$alkyl)amino, C$_{3-8}$ cycloalkylamino, C$_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle; and $R^2$ represents $C_{1-6}$alkylcarbonyl, $C_{1-6}$alkylsulfonyl, hydrogen, hydroxy, $C_{1-6}$alkyl, $C_{2-6}$alkenyl, $C_{2-6}$alkynyl, or $C_{3-8}$cycloalkyl, wherein
said alkyl, alkenyl, cycloalkyl, or alkynyl are optionally substituted by mono-, di-, or tri-halogen, hydroxy, carboxyl, nitro, cyano, $C_{1-6}$alkoxy, $C_{1-6}$alkoxycarbonyl, $C_{3-8}$cycloalkyl, amino, N-($C_{1-6}$alkyl)amino, N,N-di($C_{1-6}$alkyl)amino, N-(aryl)amino, N-(heteroaryl)amino, carbamoyl, N-($C_{1-6}$alkyl)aminocarbonyl, or N,N,-di($C_{1-6}$alkyl)aminocarbonyl.

7. The urea derivative of formula (I), its tautomeric or stereoisomeric form, or a salt thereof as claimed in claim 1,
wherein
m represents 0;
p represents 0;
—X— represents —O— or —N($R^{10}$)— (wherein $R^{10}$ is hydrogen or $C_{1-6}$ alkyl);
$R^A$ and $R^B$ represent hydrogen,
$R^1$ represents phenyl, naphthyl, pyridyl, or pyrimidyl,
wherein
said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle; and $R^2$ represents $C_{1-6}$alkylcarbonyl, $C_{1-6}$alkylsulfonyl, hydrogen, hydroxy, $C_{1-6}$alkyl, $C_{2-6}$alkenyl, $C_{2-6}$alkynyl, or $C_{3-8}$cycloalkyl, wherein
said alkyl, alkenyl, cycloalkyl, or alkynyl are optionally substituted by mono-, di-, or tri-halogen, hydroxy, carboxyl, nitro, cyano, $C_{1-6}$alkoxy, $C_{1-6}$alkoxycarbonyl, $C_{3-8}$cycloalkyl, amino, N-($C_{1-6}$alkyl)amino, N,N-di($C_{1-6}$alkyl)amino, N-(aryl)amino, N-(heteroaryl)amino, carbamoyl, N-($C_{1-6}$alkyl)aminocarbonyl, or N,N,-di($C_{1-6}$alkyl)aminocarbonyl.

8. The urea derivative of formula (I), its tautomeric or stereoisomeric form, or a salt thereof as claimed in claim 1,
wherein
m represents 1, 2, or 3;
p represents 0, 1, 2, or 3;
—X— represents a bond, —O— or —N($R^{10}$)— (wherein $R^{10}$ is hydrogen or $C_{1-6}$ alkyl);
$R^A$ and $R^B$ represent hydrogen,
$R^1$ represents phenyl, naphthyl, pyridyl, or pyrimidyl,
wherein
said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle; and $R^2$ represents hydrogen, hydroxy, $C_{1-6}$alkyl, $C_{2-6}$alkenyl, $C_{2-6}$alkynyl, or $C_{3-8}$cycloalkyl.

9. The urea derivative of formula (I), its tautomeric or stereoisomeric form, or a salt thereof as claimed in claim 1,
wherein
$R^1$ represents phenyl, naphthyl, pyridyl, or pyrimidyl,
wherein said phenyl, naphthyl, pyridyl, or pyrimidyl is optionally substituted by one or more of substituents selected from the group consisting of chloro, bromo, fluoro, nitro, methoxy, trifluoromethyl, trifluoromethoxy and $C_{1-6}$ alkanoylamino.

10. The urea derivative of the formula (I), its tautomeric or stereoisomeric form, or a salt thereof as claimed in claim 1, wherein said urea derivative of the formula (I) is selected from the group consisting of:
N-(4-chlorophenyl)-N-(3-hydroxy-1-methyl-1,2,3,4-tetrahydroquinolin-5-yl)urea;
N-[4-chloro-3-(trifluoromethyl)phenyl]-N-(3-hydroxy-1-methyl -1,2,3,4-tetrahydroquinolin-5-yl)urea;
N-[4-chloro-3-(trifluoromethyl)phenyl]-N-(3-hydroxy-1, 2,3,4-tetrahydroquinolin-5-yl) urea;
ethyl 3-({[(3-hydroxy-1-methyl-1,2,3,4-tetrahydroquinolin-5-yl)amino]carbonyl} amino)- benzoate;

N-biphenyl-3-yl-N-(3-hydroxy-1-methyl-1,2,3,4-tetrahydroquinolin-5-yl)urea, and
the salts thereof.

11. A pharmaceutical composition comprising a urea derivative of formula (I), its tautomeric or stereoisomeric form, or a physiologically acceptable salt thereof as claimed in claim 1 as an active ingredient.

12. The pharmaceutical composition as claimed in claim 11, further comprising one or more pharmaceutically acceptable excipients.

13. The pharmaceutical composition as claimed in claim 11, wherein said urea derivative of the formula (I), its tautomeric or stereoisomeric form, or a physiologically acceptable salt thereof is a VR1 antagonist.

14. The for the treatment of pain comprising administering to a subject in need thereof a therapeutically effective amount of at least one urea derivative of formula (I), its tautomeric or stereoisomeric form, or a physiologically acceptable salt thereof as claimed in claim 1.

15. The method as claimed in claim 14, wherein said pain is chronic pain, neuropathic pain, postoperative pain, or rheumatoid arthritic pain.

* * * * *